United States Patent [19]

Johnson et al.

[11] Patent Number: 5,360,797
[45] Date of Patent: Nov. 1, 1994

[54] BISPHOSPHONIC ACID DERIVATIVES USEFUL AS ANTI-ARTHRITIC AGENTS

[75] Inventors: Roy A. Johnson; Herman W. Smith, both of Kalamazoo, Mich.

[73] Assignee: The Upjohn Company, Kalamazoo, Mich.

[21] Appl. No.: 146,685

[22] Filed: Nov. 1, 1993

Related U.S. Application Data

[60] Division of Ser. No. 71,289, Jun. 1, 1993, Pat. No. 5,298,498, which is a continuation-in-part of Ser. No. 624,119, Dec. 7, 1990, abandoned.

[51] Int. Cl.$^5$ .............................................. A61K 31/66
[52] U.S. Cl. .................... 514/111; 514/102; 514/103; 514/104; 514/107; 514/110
[58] Field of Search ............... 514/104, 102, 103, 107, 514/111, 110

[56] References Cited

U.S. PATENT DOCUMENTS

| | | | |
|---|---|---|---|
| 3,683,080 | 8/1972 | Francis | 424/204 |
| 4,746,654 | 5/1988 | Breliere et al. | 514/108 |
| 4,827,010 | 5/1989 | Cadogan et al. | 558/82 |
| 5,196,409 | 3/1993 | Breuer et al. | 514/108 |
| 5,298,498 | 3/1994 | Smith | 514/111 |

FOREIGN PATENT DOCUMENTS

| | | |
|---|---|---|
| 51534/85 | 6/1986 | Australia . |
| 0085321 | 8/1983 | European Pat. Off. . |
| 0149802 | 7/1985 | European Pat. Off. . |
| 1124949 | 3/1962 | Germany . |
| 558424 | 1/1975 | Switzerland . |

OTHER PUBLICATIONS

H. Fleisch, Bone 8, Suppl. 1, pp. S23–S28 (1987).
X. Lu et al., Synthesis, pp. 848–850 (1989).
DE 3,719,513–A (Derwent 89–000580/01) (1989).
J. Meinwald et al., J. Am. Chem. Soc., 93, No. 3, pp. 725–731 (1971).
L. Ernst, J.C.S. Chem. Commun., pp. 375–376 (1977).
West German Patent DE 3,346,177, G. Pawlowski, reported in Chem. Abstracts 104:79157d. (1985).
V. A. Arbuzov and V. M. Zoroastrova, Izves., Acad. Nauk. S.S.R., (1954) 806, as reported in Chem. Abstracts 49:13222e.
R. S. Tewari et al., Indian J. Chem., 15B:753 (1977).
J. Blum and M. Zimmerman, Tetrahedron 28:275 (1972).
L. Maier and M. M. Crutchfield, Phosphorus and Sulfur 5, pp. 45–51 (1978).
C. N. Robinson and R. C. Lewis, J. Heterocyl. Chem. 10, pp. 395–397 (1973).
Chemical Abstracts (CA) 68:87351r (1968).
DE 2,245,817 as reported in Chemical Abstracts 80:146302y (1974).
DE 2,364,396 as reported in Chemical Abstracts 83:192793u (1975).
DE 2,337,845, as reported in Chemical Abstracts 81:14724y(1974).
Chemical Abstracts, vol. 68, No. 19, May 6, 1968, (Columbus, Ohio, US), V. S, Abramov et al.,: "Effect of some dihalo derivaties on sodium salts of dialkylphosphonic acids and phsophites", Chemical Abstracts 87351r, & Z.H. Obshch. Khim. 37(10), 2243–7 (1967).
L. Ernst, Org. Magnetic Resonance, 9, 35 (1977).
V. A. Arbuzo et al., Izvest. Acad. Nauk S.S.R., 1016 (1961) reported in Chemical Abstracts 55:27353a.

Primary Examiner—Marianne M. Cintins
Assistant Examiner—T. J. Criares
Attorney, Agent, or Firm—Donald L. Corneglio; Gregory W. Steele

[57] ABSTRACT

Novel acids, esters, and salts of phenyl, naphthyl, quinoxalinyl, and biphenyl bisphosphonic acids and 1,2-oxaphosphepins are described. These compounds are useful as antiinflammatory and anti-arthritic agents. Also described are known compounds of the phenyl, naphthyl, quinoxalinyl, and biphenyl bisphosphonate classes which are also useful as antiinflammatory and anti-arthritic agents. Representative compounds include [1,2-phenyldiyl]bis(methylene)bisphosphonic acid tetramethyl ester, [2,3-quinoxalindiyl]bis(methylene)bisphosphonic acid tetramethyl ester, [[3-(propyl)-4-(methoxy)-1,8-naphthalenediyl]bis(methylene)]bisphosphonic acid tetramethyl ester, [2,6-naphthalenediylbis(methylene)bisphosphonic acid tetraethyl ester, and [2,2'-biphenylenebis(methyl)]bisphosphonic acid tetramethyl ester. Representative oxaphosphepins include the preferred 3,4-dihydro-3-methoxy-7-(phenylmethoxy)-1H-naphth[1,8de][1,2]oxaphosphepin-3-oxide.

9 Claims, No Drawings

BISPHOSPHONIC ACID DERIVATIVES USEFUL AS ANTI-ARTHRITIC AGENTS

CROSS-REFERENCE TO RELATED APPLICATIONS

This application is a division of U.S. Ser. No. 08/071,289, filed Jun. 1, 1993, now U.S. Pat. No. 5,298,498 which is a continuation of International Application PCT/US91/088 17, filed Dec. 3, 1991, which is a continuation-in-part of U.S. Ser. No. 07/624,119, filed Dec. 7, 1990, abandoned.

FIELD OF THE INVENTION

This invention provides acids, esters, and salts of bisphosphonic acids and 1,2-oxaphosphepins which are useful as antiinflammatory and anti-arthritic agents.

BACKGROUND OF THE INVENTION

Among the various phosphonate derivatives known in the art are the bisphosphonates (previously known as diphosphonates) which are structurally characterized by two C-P bond The simplest bisphosphonate, 1,1-(methylene)-bisphosphonate or (gem-bisphosphonate), is a carbon surrogate of pyrophosphate. In general, it is believed that the mode of action of the bisphosphonates in vivo is analogous to the complexing ability of pyrophosphate. However, the correspondence between complexing ability and spatial relationships of the phosphonic acids has received less attention. In general, the complexing capabilities, the inhibition of crystal growth in vitro, and tissue calcification effects in vivo are considered to decline with increasing separation of the phosphonate groups. See H. Fleisch. Bone 8, (1987) Suppl. 1, S 23; X. Lu et al., Synthesis, (1989) 848, and J. Chem. Res. (S), (1978) 89.

The 1,1 class of bisphosphonates have demonstrated considerable utility in the regulation of calcification in both industrial and domestic water installations as well as in certain human diseases. Various 1,1-bisphosphonic acids have been demonstrated to inhibit the inflammation/arthritic process in the rat adjuvant arthritis model. These include hydroxyethylidine diphosphonate, dichloromethylene diphosphonate, aminopropylidine diphosphonate, 4-chlorophenylthiomethylene bisphosphonic acid (also known as SR 41319) and 2-(3-pyridinyl) ethylidinehydroxy diphosphonic acid (also known as NE 58095). A. Barbier et al., IUPHAR, 9th Int. Cong. of Pharmacology, London, (1984) Abstract 131, have shown that SR 41319 inhibits hydroxyapatite crystal deposition in arthritic rats. However, R. Roncucc: et al., Proc. Third Int. Cong. Inflam., Paris (1984) and X. Edmonds-Alt et al., Biochem. Pharmacol., (1985) 34, 4043, report that a singular mechanism for its anti-arthritic action is unlikely as cellular and immunological events are also inhibited by the drug. The foregoing studies involve the 1,1-bisphosphonic acids or their salts as do cellular studies and most biochemical studies. A selective utility of 1,1-bisphosphonate esters has been reported by L. M. Nguyen et al., J. Med. Chem., (1987) 30, 1426 with the induction of high density lipoproteins and HDL cholesterol in vivo by geminal bisphosphonate esters but not by the corresponding hemiesters or acids. An antiarthritic utility of 1,1-bisphosphonic acids and esters has been disclosed in PCT/US90/01106, filed 8 Mar. 1990, publication No. WO90/12017, 28 October 1990.

In contrast, few studies describe either chemical, biochemical, or pharmacological activities of other bisphosphonic acid derivatives. Certain 1,2-bisphosphonates have been synthesized and characterized by P. Tavs et al., Tetrahedron, (1970) 26, 5529, R. R. Irani et al. J. Phys. Chem., (1962) 66, 1349 and H. Fleisch, Bone, (1987) 8, Suppl. 1, S23 and these authors report that the complexing capabilities (Irani) as well as inhibition of crystal growth in vitro and tissue calcification (Fleisch) decline with increasing separation of the phosphonate groups. No other utilities for the 1,2-bisphosphonates have been reported.

The chemistry of the 1,3-bisphosphonates has also been reported by X. Lu et al., Synthesis, (1989) 848 and G. Sturtz et al., J. Chem. Res. (S), (1978) 89. One compound, SR 7037, a tetrabutyl ester, has been reported to have specific calcium channel inhibition properties. See, J. R. Rossier et al., J. Biol. Chem., (1989) 264, 16598.

A number of other phenyl, naphthyl, and quinoxalinyl bisphosphonic acids, and short-chain alkyl esters thereof, have also been described. The compounds are useful for spectroscopic characterization, as photo conductive compounds, as intermediates or starting materials in the synthesis of distyryl, divinyl, and diaryl benzenes, dibenzophosphepins, and isophosphindoles. Finally, certain mono- and di-N-oxides of 2,3-quinoxalinebis(methylene)bisphosphonic acid and certain esters (—$CH_3$, —$CH_2CH_3$, —CH=$(CH_3)_2$, —CH=$CHCH_2$) of these acids have been reported as being investigated for bactericidal activity.

We have discovered a series of bisphosphonates and oxaphosphepins which are useful as antiinflammatory and antiarthritic agents. The bisphosphonate series of compounds include phenyl, naphthyl, quinoxalinyl, and biphenyl bisphosphonic acids, esters, and salts thereof. Also disclosed is a series of novel oxaphosphepin compounds.

INFORMATION DISCLOSURE

U.S. Pat. No. 4,746,654 discloses bisphosphonates useful as antiinflammatory agents.

Australian Patent A-51534/85 discloses bisphosphonates useful in treating abnormal calcium and phosphorous metabolism and useful in treating arthritis.

U.S. Pat. No. 3,683,080 discloses polyphosphonates, in particular diphosphonates useful in inhibiting anomalous deposition and mobilization of calcium phosphate in animal tissue.

DE 3,719,513-A (Derwent 89-000580/01) discloses diphosphonic acid derivatives useful in treatment of disorders of calcium metabolism.

J. Meinwald et al., J. Am. Chem. Soc., 93, (1971) 725, disclose the use of [1,8-naphthylenediyl] bis(methylene)bisphosphonic acid tetramethyl ester, a 1,5 bisphosphonate, as an intermediate for Wittig reactions.

L. Ernst, J. C. S. Chem. Commun., 375 (1977), and L. Ernst, Org. Magnetic Resonance, 9:35 (1977), disclose certain ethyl esters of phenyl and naphthyl bisphosphonates. The compounds are useful in spectroscopic characterization.

R. S. Tewari et al., Indian J. Chem., 15B:753 (1977), and J. Blum and M. Zimmerman, Tetrahedron 28:275 (1972), report the use of p-xylylenebisphosphonate tetramethyl ester (Te wari) and 2,5-bis(diethylphosphonomethyl)-1,4-difluorobenzene (Blum) as intermediates in the synthesis of distyryl- and divinylbenzenes.

L. Maier and M. M. Crutchfield, Phosporus and Sulfur 5:45 (1978) disclose the synthesis of o-xylylene bisphosphonic acid and the tetramethyl ester thereof. The compounds are said to be useful as calcium and magnesium chelators.

C. N. Robinson and R. C. Lewis, J. Heterocyl. Chem. 10:395 (1973), report the synthesis of o-xylylene bisphosphonic acid, the 4-nitro analog thereof, as well as the ethyl esters of these compounds. The compounds are used as intermediates in the cyclization of arenylphosphonic acids.

Chem Abstracts (CA) 68:87351r discloses p-xylylene bisphosphonic acid and the $C_2$–$C_4$ alkyl esters thereof. No utility is reported.

DE 2,245,817, as reported in CA 80:146302y, report the 2,3,5,6-tetrachloro-p-xylylene bisphosphonic acid and the $C_1$–$C_8$ alkyl esters thereof as useful for the fireproofing of polymers.

DE 2,364,396, as reported in CA 83:192793u, reports the use of bisphosphonate ethyl esters of p-xylylene, 1,4- or 1,5-naphthalene, or 4,4'-biphenylene as starting materials in the synthesis of diquaternary aromatic salts.

DE 2,337,845, as reported in CA 81:14724y, reports the use of the methyl ester of 4,4'-bisphenylenebis(methylene)bisphospho acid as a starting material in the synthesis of fluorescent whitening agents.

DE 3,346,177, as reported in CA 104:79d, discloses a series of 2,3-bis(arylethenyl)quinoxalines as photoconductive compounds.

V. A. Arbuzov and V. M. Zoroastrova, Izves., Acad. Nauk. S.S.R., 806 (1954), as reported in Chem. Abstracts 49: 13222e, discloses [2,3-quinoxaline]bis(methylene)bisphosphonic acid, and short-chain alkyl esters thereof, and [1,4-dihydro-2,3-quinoxaline]bis(methylene)bisphosphonic acid tetraethyl ester, but do not report any utility.

V. A. Arbuzov et al., Izvest., Acad. Nauk S.S.R., 1016 (1961), as reported in Chem Abstracts 55:27353a, disclose certain mono- and di-N-oxides of 2,3-quinoxalinebis(methylene)bisphosphonic acid and certain esters (—$CH_3$, —$CH_2CH_3$, —CH=$(CH_3)_2$, —CH=$CHCH_2$) of these acids which are reportedly being investigated as bactericidal agents.

U.S. Pat. No. 4,827,101 discloses cyclic phosphonic monoesters useful in imparting heat and flame resistance to polymers. However, the reference does not suggest the oxaphosphepins of the invention.

None of the references which disclose phenyl, naphthyl, quinoxalinyl, or biphenyl bisphosphonates disclose a use as an antiarthritic or antiinflammatory agent.

SUMMARY OF THE INVENTION

This invention provides phosphonic acid derivatives of formula I wherein $R_1$, $R_2$, $R_3$, and $R_4$ may be the same or different, may form a quaternary carbon, and are hydrogen and $C_1$–$C_5$ alkyl;

A and B may be the same or different and are hydrogen, $C_1$–$C_6$ alkyl, phenyl, and $C_7$–$C_{10}$ aralkyl;

A and B taken together are $C_2$–$C_3$ cycloalkyl or the methyl-substituted derivatives thereof;

Z is substituted benzene ring of formula II, a substituted naphthalene ring of formula III, a 2,3 substituted quinoxaline ring of formula IV, and a substituted biphenyl ring of formula V;

$X_1$ and $X_2$ may be the same or different and are hydrogen, —Cl, —Br, —F, $C_1$–$C_3$ alkyl, —$OR_5$, —$(CH_2)_mCO_2A$, —$(CH_2)_mCH_2OR_5$, —$NO_2$, —$NH_2$, —$SR_6$, —$CH_2NHR_7$, and —$CH_2N(R_7)(R_8)$;

a is one or two, provided that a is one when either $X_1$ or $X_2$ is —$NO_2$;

b is one to four, provided that b is one when $X_2$ is —$NO_2$;

$R_5$ is hydrogen, $C_1$–$C_{10}$ alkyl, allyl, $C_7$–$C_6$ acyl, benzoyl, and $C_7$–$C_{10}$ aralkyl;

$R_6$ is hydrogen, $C_1$–$C_6$ alkyl, phenyl, $C_1$–$C_6$ acyl, benzoyl, and $C_7$–$C_{10}$ aralkyl;

$R_7$ and $R_8$ may be the same or different and are hydrogen, $C_1$–$C_6$ alkyl, phenyl, $C_1$–$C_6$ acyl, benzoyl, and $C_7$–$C_{10}$ aralkyl;

m is one to five;

provided, when Z is formula IIa wherein $X_2$ is hydrogen,
A and B are methyl, $C_3$–$C_6$ alkyl, phenyl, or $C_7$–$C_{10}$ aralkyl;

when Z is formula IIb wherein $X_2$ is hydrogen,
A and B are hydrogen, methyl, $C_3$–$C_6$ alkyl, phenyl, or $C_7$–$C_{10}$ aralkyl;

when Z is formula IIc wherein $X_2$ is hydrogen,
A and B are $C_5$–$C_6$ alkyl, phenyl, or $C_7$–$C_{10}$ aralkyl;

when Z is formula IIa wherein $X_2$ is —$NO_2$,
A and B are methyl, $C_3$–$C_6$ alkyl, phenyl, or $C_7$–$C_{10}$ aralkyl;

when Z is formula IIc wherein $X_2$ is 2,5-dimethyl,
A and B are hydrogen, $C_3$–$C_6$ alkyl, phenyl, or $C_7$–$C_{10}$ aralkyl:

when Z is formula IIc wherein $X_2$ is 2,5-fluoro,
A and B are hydrogen, methyl, $C_3$–$C_6$ alkyl, phenyl, or $C_7$–$C_{10}$ aralkyl;

when Z is formula IIc wherein $X_2$ is —Cl, and a is 4,
A and B are phenyl or $C_7$–$C_{10}$ aralkyl;

when Z is formula IIIa wherein $X_1$ and $X_2$ are both hydrogen,
A and B are hydrogen, $C_2$–$C_6$ alkyl, phenyl, or $C_7$–$C_{10}$ aralkyl;

when Z is formula III c-f, i, j wherein $X_1$ and $X_2$ are both hydrogen,
A and B are hydrogen, $C_3$–$C_6$ alkyl, phenyl, or $C_7$–$C_{10}$ aralkyl;

when Z is formula IV wherein $X_2$ is —Cl or methyl,
A and B are phenyl or $C_7$–$C_{10}$ aralkyl;

when Z is formula Vi wherein $X_1$ and $X_2$ are both hydrogen,
A and B are hydrogen, $C_3$–$C_6$ alkyl, phenyl, or $C_7$–$C_{10}$ aralkyl;

when Z is formula Ve wherein $X_1$ and $X_2$ are both hydrogen,
A and B are $C_1$–$C_6$ alkyl, phenyl, or $C_7$–$C_{10}$ aralkyl;

or the pharmacologically acceptable salts thereof.

The preferred bisphosphonates of this aspect of the invention are [[4-(octyloxy)-1,8-naphthalenediyl]bis(methylene)]bisphosphonic acid tetramethyl ester, [[4-phenylmethoxy)-1,8-naphthalenediyl]bis(methylene)]-bisphosphonic acid tetramethyl ester, [[3,6-(dimethoxy)-1,8-naphthalenediyl]bis(methylene)]bisphosphonic acid tetraethyl ester, [[3-(propyl)-4-(methoxy)-1,8-naphthalenediyl]bis(methylene)]bisphosphonic acid tetramethyl ester, and [1,4-naphthalenediylbis(methylene)]-bisphosphonic acid tetramethyl ester. Most preferred is [1,4-naphthalenediylbis(methylene)]bisphosphonic acid tetramethyl ester.

This invention also provides a compound of formula VII wherein A is hydrogen, $C_1$–$C_6$ alkyl, phenyl, and $C_7$–$C_{10}$ aralkyl;

$X_1$ and $X_2$ may be the same or different and are hydrogen, —Cl, —Br, —F, $C_1$–$C_3$ alkyl, —$OR_5$, —$(CH_2)$-

$_mCO_2A$, —$(CH_2)_mCH_2OR_5$, —$NO_2$, —$NH_2$, —$SR_6$, —$CH_2NHR_7$, and —$H_2N(R_7)(R_8)$;

a is one or two, provided that a is one when either $X_1$ or $X_2$ is —$NO_2$;

$R_5$ is hydrogen, $C_1$–$C_{10}$ alkyl, allyl, $C_1$–$C_6$ acyl, benzoyl, and $C_7$–$C_{10}$ aralkyl;

$R_6$ is hydrogen, $C_1$–$C_6$ alkyl, phenyl, $C_1$–$C_6$ acyl, benzoyl, and $C_7$–$C_{10}$ aralkyl;

$R_7$ and $R_8$ may be the same or different and are hydrogen, $C_1$–$C_6$ alkyl, phenyl, $C_1$–$C_6$ acyl, benzoyl, and $C_7$–$C_{10}$ aralkyl;

m is one to five;

or the pharmacologically acceptable salts thereof.

The preferred 1,2-oxaphosphepins of this aspect of the invention are 3,4-dihydro-3-methoxy-7-(phenylmethoxy)-1H-naphth[1,8de][1,2]oxaphosphepin 3-oxide, 3,4-dihydro-3-ethoxy-7-(phenylmethoxy)-1H-naphth[1,8de][1,2]oxaphosphepin 3-oxide, 3,4-dihydro-3,6,9-trimethoxy-1H-naphth[1,8de][1,2]oxaphosphepin 3-oxide, 3,4-dihydro-3-methoxy-1H-naphth[1,8de][1,2]oxaphosphepin 3-oxide. The compound 3,4-dihydro-3-methoxy-7-(phenylmethoxy)-1H-naphth[1,8de][1,2]oxaphosphepin 3-oxide is most preferred.

The invention also provides a use of a compound of formula I for the manufacture of a medicament for use in treating arthritic disease and disease characterized by chronic inflammatory immunopathological mechanisms wherein $R_1$, $R_2$, $R_3$, and $R_4$ may be the same or different, may form a quaternary carbon, and are hydrogen and $C_1$–$C_5$ alkyl;

A and B may be the same or different and are hydrogen, $C_1$–$C_6$ alkyl, phenyl, and $C_7$–$C_{10}$ aralkyl;

A and B taken together are $C_2$ cycloalkyl, $C_3$ cycloalkyl, or the alkyl-substituted derivatives thereof;

Z is a substituted benzene ring of formula II, a substituted naphthalene ring of formula III, a 2,3 substituted quinoxaline ring of formula IV, and a substituted biphenyl of formula V;

$X_1$ and $X_2$ may be the same or different and are hydrogen, —Cl, —Br, —F, $C_1$–$C_3$ alkyl, —$OR_5$, —$(CH_2)_mCO_2A$, —$(CH_2)_mCH_2OR_5$, —$NO_2$, —$NH_2$, —$SR_6$, —$CH_2NHR_7$, and —$CH_2N(R_7)(R_8)$;

a is one or two, provided that a is one when either $X_1$ or $X_2$ is —$NO_2$;

b is one to four, provided that b is one when $X_2$ is $NO_2$;

$R_5$ is hydrogen, $C_1$–$C_{10}$ alkyl, allyl, $C_1$–$C_6$ acyl, benzoyl, and $C_7$–$C_{10}$ aralkyl;

$R_6$ is hydrogen, $C_1$–$C_6$ alkyl, phenyl, $C_1$–$C_6$ acyl, benzoyl, and $C_7$–$C_{10}$ aralkyl;

$R_7$ and $R_8$ may be the same or different and are hydrogen, $C_1$–$C_6$ alkyl, phenyl, $C_1$–$C_6$ acyl, benzoyl, and $C_7$–$C_{10}$ aralkyl;

m is one to five;

or the pharmacologically acceptable salts thereof.

The preferred bisphosphonates of this aspect of the invention are [1,4-phenylenebis(methylene)bisphosphonic acid tetramethyl ester, [1,4-naphthalenediylbis(methylene)]bisphosphonic acid tetramethyl ester, and [2,6-naphthalenediylbis(methylene)]bisphosphonic acid tetraethyl ester.

The invention also provides a use of a compound of formula VII for the manufacture of a medicament for use in treating arthritic disease and disease characterized by chronic inflammatory immunopathological mechanisms.

Most particularly, the invention provides a pharmaceutical composition comprising the compounds 3,4-dihydro-3-methoxy-7-(phenylmethoxy)-1H-naphth[1,8de][1,2]oxaphosphepin 3-oxide, 3,4-dihydro-3-ethoxy-7-(phenylmethoxy)-1H-naphth[1,8de][1,2]oxaphosphepin 3-oxide, 3,4-dihydro-3,6,9-trimethoxy-1H-naphth[1,8de][1,2]oxaphosphepin 3-oxide, or 3,4-dihydro-3-methoxy-1H-naphth[1,8de][1,2]oxaphosphepin 3-oxide; 3,4-dihydro-3-methoxy-7-(phenylmethoxy)-1H-naphth[1,8de][1,2]oxaphosphepin 3-oxide is most preferred in a pharmaceutical composition.

This invention also provides a method of treating humans with an effective amount of a compound of formula I wherein $R_1$, $R_2$, $R_3$, and $R_4$ may be the same or different, may form a quaternary carbon, and are hydrogen and $C_1$–$C_5$ alkyl;

A and B may be the same or different and are hydrogen, $C_1$–$C_6$ alkyl, phenyl, and $C_7$–$C_{10}$ aralkyl;

A and B taken together are $C_2$–$C_3$ alkyl or the methyl-substituted derivatives thereof;

Z is substituted benzene ring of formula II, a substituted naphthalene ring of formula III, a 2,3 substituted quinoxaline ring of formula IV, and a substituted biphenyl ring of formula V;

$X_1$ and $X_2$ may be the same or different and are hydrogen, —Cl, —Br, —F, $C_1$–$C_3$ alkyl, $OR_5$, —$(CH_2)_mCO_2A$, —$(CH_2)_mCH_2OR_5$, —$NO_2$, —$NH_2$, —$SR_6$, —$CH_2NHR_7$, and —$CH_2N(R_7)(R_8)$;

a is one or two, provided that a is one when either $X_1$ or $X_2$ is —$N_2$;

b is one to four, provided that b is one when $X_2$ is $NO_2$;

$R_5$ is hydrogen, $C_1$–$C_{10}$ alkyl, allyl, $C_1$–$C_6$ acyl, benzoyl, and $C_7$–$C_{10}$ aralkyl;

$R_6$ is hydrogen, $C_1$–$C_6$ alkyl, phenyl, $C_1$–$C_6$ acyl, benzoyl, and $C_7$–$C_{10}$ aralkyl;

$R_7$ and $R_8$ may be the same or different and are hydrogen, $C_1$–$C_6$ alkyl, phenyl, $C_1$–$C_6$ acyl, benzoyl, and $C_7$–$C_{10}$ aralkyl;

m is one to five;

as a treatment of human inflammatory, granulomatous, calcemic, atherosclerotic, and hypertensive disease. This invention further provides a method of treating humans with an effective amount of a compound of formula VII as a treatment of human inflammatory, granulomatous, calcemic, atherosclerotic, and hypertensive disease.

Additional, and particularly preferred, utilities for the compounds of the invention are for the treatment of inflammation and arthritic disease and diseases characterized by chronic inflammatory immunopathological mechanisms. Most particularly, this invention provides the compounds [1,4-phenylenebis(methylene)bisphosphonic acid, tetramethyl ester, [1,4-naphthalenediylbis(methylene)]bisphosphonic acid tetramethyl ester, [2,6-naphthalenediylbis(methylene)]bisphosphonic acid tetraethyl ester, 3,4-dihydro-3-methoxy-7-(phenylmethoxy)-1H-naphth[1,8de][1,2]oxaphosphepin 3-oxide, 3,4-dihydro-3-ethoxy-7-(phenylmethoxy)-1H-naphth[1,8de][1,2]oxaphosphepin 3-oxide, 3,4-dihydro-3,6,9-trimethoxy-1H-naphth[1,8de][1,2]oxaphosphepin 3-oxide, or 3,4-dihydro-3-methoxy-1H-naphth[1,8de][1,2]oxaphosphepin 3-oxide as a treatment of inflammation and to relieve symptoms of arthritis. The compound 3,4-dihydro-3-methoxy-7-(phenylmethoxy)-1H-naphth[1,8de][1,2]oxaphosphepin 3-oxide is most preferred as a treatment of inflammation and to relieve symptoms of arthritis.

DETAILED DESCRIPTION

The compounds of the invention in which $R_1$, $R_2$, $R_3$, and $R_4$, are hydrogen are preferred. If substituted, it is preferred that one of $R_1$ or $R_2$ and one of $R_3$ or $R_4$ be alkylated; methyl is preferred as the alkyl derivative. The methyl phosphonate esters are preferred with the tetramethyl esters being most preferred. The methyl ester of the oxaphosphepin is most preferred.

When used as a pharmaceutical formulation, it is possible to modify the compounds of the invention into forms suitable for administration. Administration may be accomplished by any number of means, including, but not limited to, oral, anal, buccal, intravenous, subcutaneous, intramuscular, topical, or aerosol. In any pharmaceutical formulation, at least one compound of the invention and/or one of its pharmacologically acceptable salts are mixed or combined with at least one carrier or vehicle. Carriers or vehicles include inorganic or organic substances which are suitable for administration and which do not react with the new compounds. Examples of suitable carrier vehicles include water, vegetable oils, benzyl alcohols, polyethylene glycols, gelatine, carbohydrates such as lactose or starch, magnesium stearate, talc, and vaseline. In particular, tablets, coated tablets, capsules, syrups, liquids, drops, or suppositories are used for oral, anal, or buccal applications. When injection or parenteral is the route of administration solutions of an oily or aqueous nature are preferred, but suspensions, emulsions, or implants may be used as well. Ointments, creams, or powders are used for topical administration, and any suitable aerosol form for inhalation therapy. It is also possible to sterilize and/or lyophilize these compounds for subsequent use in the preparation of products.

The formulations may also contain one or more pharmacologically acceptable auxiliaries, such as lubricants, preservatives, stabilizers, wetting agents, emulsifiers, salts, buffers, colorants, flavorings, and aromatic substances.

The invention also relates to the use of the compounds of the invention and their pharmacologically acceptable salts for the therapeutic treatment of human inflammatory, granulomatous, calcemic, atherosclerotic, and hypertensive disease. Particularly preferred utilities are for the treatment of inflammation and arthritis. As a general rule the pharmaceutical compositions of the present invention are administered in doses similar to known and commercially available products, such as the antiarthritic and antiinflammatories, e.g., phenylbutazone, indomethacin, gold sodium thiomulate, dexamethasone, penicillamine. sodoxicam, and naproxen. The preferred method of administration is orally at about 2 to 100 mg, administered 1–6 times a day. The preferred dose is between about 0.01 to 10 µg/kg/min when by intravenous infusion about 0.5 to 10 mg, intravenously. The preferred daily dose is about 0.03–85 mg/kg body weight. However, the specific dose for a patient depends on a wide variety of factors, for example on the efficacy of the specific compound employed (alone or when used in combination with other medicaments), the severity of the disorder for which therapy is sought, on the age, weight, health, sex, and diet of the patient, on the method of administration, and on the excretion rate.

Terms used in this specification and claims have the following definitions:

"1,2-bisphosphonate" means a bisphosphonate in which one phosphonate group is separated from the second by a carbon chain two carbons in length. Similarly, a "1,3-bisphosphonate" has a three atom separation, a "1,4-bisphosphonate" has a four atom separation, a "1,5-bisphosphonate" has a five atom separation, etc.

The carbon atom content of the various hydrocarbon-containing moieties is indicated by designating the minimum and maximum number of carbon atoms in the moiety, i.e. $C_m$–$C_n$ indicates a moiety of integer "m" to the integer "n" carbon atoms, inclusive, and encompasses isomeric forms. For example, $C_1$–$C_6$ alkyl refers to an alkyl of one to six carbons, inclusive, including the isomeric forms.

"Allyl" means —$CH_2$—CH=$CH_2$.

"Benzyl" means ($C_6H_5$)$CH_2$—.

"Benzoyl" means the compound formed by the loss of the hydroxyl from benzoic acid, i.e. ($C_6H_5$)CO—.

"Acyl" means the compound formed by the loss of the hydroxyl from an aliphatic carboxylic acid, e.g. $CH_3$—$CH_2$-CO—.

"Aralkyl" means an alkyl-substituted benzene ring.

Throughout the disclosure and claims, common shorthand chemical terms are used.

Temperatures are in degrees Celsius.

The letter "h" means hours.

The term "NMR ($CDCl_3$)δ" means proton nuclear magnetic resonance spectral analysis in delta scale units.

"IR" means infrared spectral analysis.

"UV" means ultraviolet spectral analysis.

"MS" means mass spectral analysis in mass to charge ratio.

"TLC" means thin layer chromatography.

Synthesis of Representative Compounds

In preparative methods which follow, the compounds of the invention are synthesized following techniques which are known, or readily acquired, by one skilled in the art. Examples of such techniques are:

J. Tyman, et al., Synthetic Communications, (1989) 19, 179 (synthesis of substituted naphthalic anhydrides);

E. D. Bergmann et al., J. Am. Chem. Soc., (1953) 75, 2760, J. Cason et al., J. Org. Chem., (1973) 38, 1944, J. Cason et al., J. Org. Chem., (1968) 33, 3404, and R. H. Mitchell et al., Tetrahedron, (1968) 24, 1397 (reductions of naphthalic anhydride to naphthalene bismethanols);

R. H. Mitchell et al., Tetrahedron, (1968) 24, 1397 (preparation of dibromomelhylnaphthalenes);

J. Meinwald et al., J. Am. Chem. Soc., (1971) 93, 725 (reaction of dibromethylnaphthalenes to naphthalene bismethylene disphosphonates);

C. N. Robinson and R. C. Lewis, J. Heterocyclic Chem., (1973) 10, 395, J. R. Wiseman et al., J. Org. Chem., (1980) 45, 5 16, and G. M. Rubottom and J. E. Way, Synthetic Communications, (1984) 14, 507 (synthesis of substituted xylenes);

J. R. Wiseman et al., J. Org. Chem. (1980) 45,516 and E. F. M. Stephenson. Organic Synthesis Coll., Vol. II, 984 (bromination of substituted xylenes);

L. Ernst, Org. Magnetic Resonance, (1977) 9, 35, and L. Ernst, J. C. S. Chem. Commun. (1977) 375 (spectroscopic properties of methylenephosphonates);

L. M. Nguyen et al., J. Meal. Chem. (1987) 30, 1426 (hydrolysis/esterification); and J. Petrova et al., Synthesis, (1975) 658 and A. F. Kluge, Tetrahedron Letters, (1978) 39, 3629 (methylene alkylation).

All starting materials are known and are commercially available, or are readily prepared from known or readily available starting materials. Dibromomethylene compounds are available from the Aldrich Company, Milwaukee, Wis.

The synthesis of compounds of the invention proceed, generally, as outlined below and, more specifically, in the examples that follow. The synthesis is outlined in Chart A where the $X_1$ and $X_2$ radicals are omitted.

For compounds of the 1,8-naphthalene and 1,2-oxaphosphepin series, naphthalic anhydride (Chart A (1)) or substituted naphthalic anhydrides, e.g. 2-chloro, 3-bromo, 4-bromo, etc., serve as the starting materials. Proceeding from Chart A(1) to A(2), the anhydride (1) is reduced first, to the corresponding dimethanol and in a second step, to the dibromide (2). As an alternative, some dibromides, e.g. 1,8-bis(bromomethyl)naphthalene, may be obtained from commercial vendors. In the presence of an organic solvent, the dibromide (2) is reacted with limited, e.g., 1 mole equivalent, trialkyl phosphite compounds to provide, via Arbuzov-type reactions, the oxaphosphepin esters (3) and, using excess trialkyl phosphite, the bisphosphonate esters (4). These products are useful as end products or may be further modified as described below. These reactions are carried out under ambient to reflux temperature conditions. e.g. 25 to 130 degrees, for a time sufficient to effect as complete a reaction as possible, e.g. from 3 to 48 hours.

The ester groups of the bisphosphonate (Chart. A(4)) may be hydrolyzed by any volatile mineral acid, e.g. hydrochloric or hydroobromic, to the tetra-acid (5) or the ester groups are selectively removed with bromotrimethyl silane to provide mono-, di- and tri-acids. The di-acid is shown in Chart A(6). The mono-, di-, and tri-acids are conveniently separated by reversed phase chromatographic techniques known by those skilled in the art. Esterification of the di-acid (6), and, similarly the mono- or tri-acids, with a second ester group (Chart A(7)) is achieved conveniently with an orthacid or diazoalkane; the diazoalkane, e.g. diazomethane, is believed to be most useful in esterification of sterically hindered acids. Alkylation of the tetra-acid (5) or the (bismethylene)bisphosphonate (7), via mono- or bis-carbanions generated with alkali metal alkoxide, e.g., butyl lithium or lithium amides, or an alkali metal hydride reagent, is done using alkyl halides, preferably iodide or bromide, and produces the C-alkyl tetra-acid (Chart A(8.1)) and ester derivatives (8.2).

The quinoxaline compounds may be synthesized by reacting 1,2-diaminobenzene, or a substituted diaminobenzene, with a 1,4-dibromo-α-diketone to produce the corresponding bis(bromomethyl)quinoxaline. Alternatively, bis(bromomethyl)quinoxaline may be obtained commercially. The quinoxaline dibromide is used to produce the esterified and alkylated quinoxaline compounds of the invention following the scheme as outlined above.

Finally, the remaining substituted naphthalenes and substituted benzenes of the invention are produced using corresponding dibromomethylenes as starting materials using synthetic techniques as described above or, alternatively, frown commercial sources. Substituted o-xylene derivatives are also synthesized using known techniques or purchased commercially. The esterification and alkylation of these compounds is also accomplished following the above procedure.

As each step of the synthesis is completed, the reaction mixture can be treated by conventional chemical processing procedures, e.g., by dilution, solvent partitioning, filtration, concentration, and cooling, to separate the products from the reactants and solvents. The solid compounds of the invention have melting points generally in the range of about 50 to greater than 250 degrees, and thus are easily separated by filtration or centrifugation; oils or liquids are separated by chromatographic methods. Solids may be obtained in purer form by recrystallization from hot organic solvents; liquids and oils are further puried by chromatographic methods or distillation.

The conditions described here and in the examples that follow for the synthesis and purification of the compounds of the invention may be altered depending on the choice of reactants and solvents, the batch size, the degree to which the reaction is to be carried to completion, and other factors of concern to the chemist.

By following the preceding description, and without further elaboration, one skilled in the art can utilize the present invention to the fullest extent. The representative examples and demonstrations of utility that follow are merely illustrative, and not limiting, of the disclosure.

Preparation 1

1,8 -dibromomethylene-4-benzyloxynaphthalene 4-sulfonaphthalic anhydride (Orlex Chemical Corp., Fairlawn, N.J.) or the corresponding potassium salt (Aldrich Chemical Co., Milwaukee, Wis.) is fused with molten potassium hydroxide, cooled, and acidified. The resulting 4-hydroxynaphthalic anhydride is removed by filtration and treated with one equivalent of potassium carbonate and benzyl bromide to obtain 4-benzyloxy naphthalic anhydride. Lithium tetrahydride aluminate (lithium aluminum hydride) reduction in tetrahydrofuran for 3 h at reflux temperatures gives the 1-8-naphthalenedimethanol. A suspension of the dimethanol (1.3 g, 5.0 mmol) in toluene (15 ml) is treated with a solution of phosphorous bromide (0.7 ml, 0.2 g, 7.5 mmol) in methylene chloride (7.5 ml) during 20–30 minutes and reacted for an hour. The solution is poured into ice-water, diluted with ethyl acetate, partitioned, and the organics are washed with 5% sodium chloride solutions. Drying and evaporation of solvent gives a crystalline residue (1.94 g) which deposits 1,8-dibromomethylene-4-benzyloxynaphthalene (1.3 g, m.p. 59°–60° C.) from hexane solution.

Preparation 2

1,8-dibromomethylene-4-(8-octyloxy)naphthalene

A suspension of 4-(8-octyloxy)-1,8-naphthalene dimethanol (3.8 g, 12 mmol) in toluene (50 ml) is treated with pyridine (0.14 ml) and a solution of $PBr_3$ (2.0 ml, 24 mmol) in methyl chloride (25 ml) is added during 30 minutes. The solution is reacted at ambient temperature for 3 hours. The solution is diluted with ethyl acetate, washed with 5% sodium carbonate and 5% sodium chloride solutions, dried and, evaporated. The residue is crystallized from acetonitrile to yield 1,8-dibromomethylene-4-(8-octyloxy)naphthalene (2.62 g, m.p. 54°–55° C.).

IR (mull) 1585, 1515, 1415, 1355, 1330, 1280, 1250, 1230, 1200, 1190, 1160, 1135, 1090, 1050, 1025, 825, and 765 cm$^{-1}$. MS m/z 442, 440 (M+), 363, 361, 282, 251, 249, 183, 172, 170, 153, 141, and 115. NMR (CDCl$_3$) δ0.89 (t, J=6.8Hz, 3, CH$_3$), 1.35 (m, 8, CH$_2$), 1.54 (m, 2, CH$_2$), 1.92 (m, 2, CH$_2$), 4.12 (t, J=6.4Hz, 2, CH$_2$), 5.31 (s, 2, CH$_2$), 6.78 (d, J=8.1Hz, 1, ArH), 7.45 q, J=7.1, 8.4Hz, 1, ArH), 7.53 (d, J=8.1Hz, ArH), 7.63 (q, J=1.5, 7.1Hz, 1, ArH), 8.46 (q, J=1.5, 8.4Hz, 1, ArH). Anal. Calc'd for C$_{20}$H$_{26}$Br$_2$O: C, 54.31; H, 5.92; Br, 36.14. Found: C, 54.63; H, 6.05; Br, 35.30.

Preparation 3

1,8-dibromomethylene-4-methoxy-3-propylnaphthalene

A suspension of 3-propyl-4-methoxy-1,8-naphthalene dimethanol (1.3 g, 5.0 mmol) in toluene (15 ml) is treated with a solution of phosphorous bromide (0.7 ml, 0.2 g. 7.5 mmol) in methylene chloride (7.5 ml) during 20–30 minutes and reacted for an hour. The solution is poured into ice-water, diluted with ethyl acetate, partitioned, and the organic please is washed with 5% sodium chloride solutions. Drying and evaporation of solvent gives a residue (1.94 g) which deposited 1,8-dibromomethylene-4-methoxy-3-propylnaphthalene (1.3 g, m.p. 59°–60° C.) from hexane solution.

IR (mull) 1570, 1500, 1360, 1280, 1255, 1220, 1195, 1155, 1080, 1010, 910, 885, 825, and 775 cm$^{-1}$. MS m/z 386, 384 (M+), 307, 305, 226, 211, 197, 183, 169, 167, 165, 153, 152, 141, 139 and 115. NMR (CDCl$_3$) δ0.98 (t, J=7.5Hz, 3, CH$_3$), 1.71 (m, 2, CH$_2$), 2.76 (t, J=7.5Hz, 2, CH$_2$), 3.91 (s, 3, CH$_3$), 5.29, 5.27 (s, 4, CH$_2$), 7.47 (m, 2, ArH), 7.57 (d, J=7.9Hz, 1, ArH), 8.29 (d, J=7.9Hz, 1, ArH). Anal. Calc'd for C$_{16}$H$_{18}$Br$_2$O: C, 49.76; H, 4.69; Br, 41.39. Found: C, 49.80; H, 4.73; Br, 40.81.

EXAMPLE 1

[8-(bromomethyl)-4-(phenylmethoxy)-1-naphthyl]-methyl phosphonic acid dimethyl ester A suspension of 1,8-dibromomethylene-4-benzyloxynaphthalene (Preparation 1, 17.15 g. 41 mmol) in toluene (120 ml) is treated with trimethylphosphite (11.5 ml, 12.1 g, 98 mmol) and heated at reflux temperature for 4.5 hours. A 1.0 g aliquot of the product is fractionated on silica gel (75 g) with ethyl acetate eluent. Fractions containing [8-(bromomethyl)-4-(phenylmethoxy)-1-naphthyl]methyl-phosphonic acid dimethyl ester (60 mg) and 3,4-dihydro-3-methoxy-7-(phenylmethoxy)-1H-naphth [1,8-de][1,2] oxaphosphepin 3-oxide (0.33 g) which contained 25–35% 3,4-dihydro-3-methoxy-8-(phenylmethoxy)-1H-naphth [1,8-de][1,2] oxaphosphepin 3-oxide are collected. The fraction eluted with 5% methanol gives pure [[4-phenylmethoxy)-1,8-naphthalenediyl]bis (methylene)]bisphosphonic acid tetramethyl ester (0.42 g). The remainder of the reaction mixture is reserved for further purification.

IR (mull) 1595, 1425, 1350, 1285, 1230, 1210, 1190, 1160, 1080, 1055, 875, 855, 825, 765, 745, 725 and 700 cm$^{-1}$. NMR (CDCl$_3$) δ3.61 (d, J=10.7Hz, 3, OCH$_3$), 3.99 (d, J=21Hz, 2, CH$_2$), 5.23 (s, 2, CH$_2$), 5.26 (s, CH$_2$), 6.90 (d, J=8.0 Hz, 1, ArH), 7.25–7.58 (m, 8, ArH), 8.49 (dd, J=1.30, 8.5Hz, 1, ArH).

EXAMPLE 2

[[4-phenylmethoxy)-1,8-naphthalenediyl]bis(methylene)]bisphosphonic acid tetramethyl ester The remaining reaction mixture from Example 1 is treated with additional trimethylphosphite (20 g, 161 mmol) and heated at reflux temperature for an additional 3 hours. The cooled solution is evaporated and the residue triturated with ether, then recrystallized from toluene to provide [[4-phenylmethoxy)-1,8-naphthalenediyl]bis (methylene)]bisphosphonic acid tetramethyl ester (4.0 g). The recrystallized fractions are again reserved for further purification.

IR (mull) 1600, 1515, 1415, 1360, 1320, 1280, 1250, 1220, 1185, 1160. 1055, 1035, 905, 865, 805, 770, 735, and 700 cm$^{-1}$. MS m/z 378 (M+) 369, 355, 337, 323, 277, 263, 245, 229, 168, 151, 141, 139, 115, 109, and 91. NMR (CDCl$_3$) δ3.59 (d, J=12.7 Hz, 12, OCH$_3$), 3.99 (d, J=20.2Hz, 2, CH$_2$—P) 4.06 (d, J=20.2 Hz, 2, CH$_2$—P), 5.23 (s, 2, CH$_2$—O), 6.86 (d, J=8.1 Hz, 1, ArH), 7.42 (m, 5, ArH), 7.51 (m, 3, ArH), 8.45 (m, 1, ArH). Anal. Calc'd for C$_{23}$H$_{28}$O$_7$P$_2$: C, 57.74; H, 5.90; P, 12.94. Found: C, 57.91; H, 6.11, P, 12.82.

EXAMPLE 3

3,4-dihydro-3-methoxy-7-(phenylmethoxy)-1H-naphth [1,8-de][1,2]oxaphosphepin 3-oxide The combined crystallization filtrates from Example 2 are evaporated and the residue is purified on silica gel (500 g) to yield a 3:1 ratio of the 7-phenylmethoxy and 8-phenylmethoxy oxaphosphepins, (total mass of 3.75 g, m.p. 129°–130° C.) after toluene crystallization and an additional 9.8 g of [[4-phenylmethoxy)-1,8-naphthalenediyl]bis (methylene)]bisphosphonic acid tetramethyl ester (m.p. 123-124) after toluene crystallization.

IR (mull) 1595, 1425, 1280, 1265, 1250, 1235, 1185, 1155, 1065, 1025, 1010, 870, 855, 830, 815, 775, 730, and 700 cm$^{-1}$. MS m/z 354(M+), 263, 245, 231, 202, 185, 169, 141, 139, 128, 115 and 91. NMR (CDCl$_3$) δ3.72*, 3.73 (d, J=10.8 Hz, 3, OCH$_3$), 3.75–3.99 (m, 2, CH$_2$—P) 5.22, 5.24* (s, 2, CH$_2$—C$_6$H$_5$), 5.39 (q, J=13.8, 18.6 Hz, 1, CH—O—), 5.49 (q, J=13.8, 17.2 Hz, 1, CH—O—), 6.79* (d, J=8.1Hz, 0.25–0.33, ArH), 6.85 (dd, J=1.18, 8.1Hz, 0.66–0.75, ArH), 7.25 (dd, J=2.58, 8.1Hz, 0.6–0.75, ArH), 7.28* (d, J=8.1Hz, 0.25–0.33, ArH), 7.35–7.51 (m, 7, ArH), 8.39–8.48 (m, 1, ArH). Anal. Calc'd for C$_{20}$H$_{19}$O$_4$P: C, 67.79; H, 5.40, P, 8.68. Found: C, 67.98; H, 5.49; P, 8.60.

EXAMPLE 4

[8-(bromomethyl)-4-(phenylmethoxy)-1-naphthyl]-methyl phosphonic acid diethyl ester A suspension of 1,8-dibromo-4-benzyloxynaphthalene (Preparation 1, 4.2 g, 10 mmol) in toluene (25 ml) is treated with triethylphosphite (4.1 ml), 3.98 g, 24 mmol) and heated at reflux temperature for 45 hours. The solution is evaporated and the residue (6.0 g) is purified on silica gel (300 g). The monophosphonate [8-(bromomethyl)-4-(phenylmethoxy)-1-naphthyl]methyl phosphonic acid diethyl ester (0.41 g) elutes with 7:3 hexane:ethyl acetate.

IR (mull) 1595, 1360, 1290, 1250, 1215, 1195, 1170, 1040, 980, 875, 845, 825, 800, 775, 750, and 700 cm$^{-1}$. MS m/z 476, 478 (M+), 387, 384, 368, 341,306, 278, 251,250, 249, 169, 141, 108, 106, and 91. NMR (CDCl$_{13}$) δ1.37 (t, J=7.07 Hz, 3, CH$_3$), 4.93 (m, 4, CH$_2$P—, O—CH$_2$—CH$_3$), 5.24 (s, 2, CH$_2$), 5.28 (s, 2, CH$_2$), 6.90 (d, J=8Hz, 1, ArH), 7.26–7.57 (m, 8, ArH), 8.45 (dd, J=1,4, 8.5Hz, 1, ArH). Anal. Calc'd for C$_{23}$H$_{26}$BrO$_4$P: C, 57.87; H, 5.49; Br, 16.74; P, 6.48. Found: C, 57.68; H, 5.50; Br, 16.83, P, 6.57.

EXAMPLE 5

3,4-dihydro-3-ethoxy-7-(phenylmethoxy)-1H-naphth[1,8-de][1,2]oxaphosphepin 3-oxide Following the procedure of Example 4, and subsequent to the elution of the monophosphonate (Example 4), (3,4-dihydro-3-ethoxy-7-(phenylmethoxy)-1H-naphth [1,8de][1,2]oxaphosphepin 3 -oxide and 3,4-dihydro-3 -ethoxy-8-(phenylmethoxy) -1H-naphth [1,8 de][1,2]oxaphosphepin 3-oxide) elute with 95:5 ethyl acetate:methanol. The phosphepins are recovered in a ratio of 9:1, 0.40 g total, m.p. 120°-121° C. after ethyl acetate-hexane crystallization.

IR (mull) 1600, 1295, 1275, 1245, 1195, 1160, 1070, 1030, 1020, 990, 875, 850, 825, 785, and 750 cm$^{-1}$. NMR (CDCl$_3$) $\delta$1.24 (t, J=7Hz, 3, CH$_3$), 3.75 (q, J=17, 19Hz, 1, CH), 3.81 (q, J=17, 19 Hz, 1, CH), 4.09 (m, 2, CH$_2$—CH$_3$), 5.23 (s, 2, CH$_2$—C$_6$H$_5$), 5.40 (q, J=13.9, 18.5 Hz, 1, CH—P—), 5.50 (q, J=13.9, 17.3 Hz, 1, CH—P—), 6.80 (d, J=7.9 Hz, 1, ArH), 7.25 (dd, J=2.4, 7.9 Hz, 1, ArH), 7.35-7.51 (m, 7, ArH), 8.46 (m, 1, ArH).

Resonances at $\delta$5.24 (s, CH$_2$-C$_6$H$_5$), 6.79 (d, J=7.9) corresponded to approximately 10% 3,4-dihydro-3-ethoxy-8-(phenylmethoxy)-1H-naphth[1,8-de][1,2]-oxaphosphepin 3-oxide. MS m/z 368 (M$^+$), 277, 249, 231,203, 202, 169, 141, 139, 128, 115, and 91. Anal. Calc'd for C$_{21}$H$_{21}$O$_4$P: C, 68.47; H, 5.74; P, 8.40. Found: C, 67.83; H, 5.79; P, 8.40.

EXAMPLE 6

[[4-phenylmethoxy)-1,8-naphthalenediyl]bis(methylene)]bisphosphonic acid tetraethyl ester Following the procedure of Examples 4 and 5, and subsequent to the elution of the compounds of Examples 4 and 5, the bisphosphonate ([[4-phenylmethoxy)-1,8-naphthalenediyl]bis(methylene)]bisphosphonic acid tetraethyl ester) is eluted with 9:1 ethyl acetate:methanol. The title compound is recovered after hexane crystallization (4.82 g, m.p. 75°-76° C.).

IR (mull) 1595, 1415, 1345, 1275, 1240, 1215, 1155, 1055, 1020, 975,955, 865, 850, 830, 780, 755, 720 and 705 cm$^{-1}$. MS m/z 534(M$^+$), 443, 415, 397, 331, 307, 300, 279, 251, 168, 141, 115, and 91. NMR (CDCl$_3$) $\delta$1.16, 1.17 (t, J=7.1Hz, 3, CH$_3$), 3.94 (m, 12, CH$_2$—P—, OCH$_2$CH$_3$), 5.23 (s, 2, CH$_2$), 6.84 (d, J=8.0Hz, 1, ArH), 7.39-7.51 (m, 8, ArH), 8.43 (m, 1, ArH). MS m/z 534(M$^+$), 443, 415, 397, 331, 307, 300, 279, 251, 167, 141, 115, and 91. Anal. Calc'd for C$_{27}$H$_{36}$O$_7$P$_2$: C, 60.67; H, 6.79; P, 11.59. Found: C, 60.08; H, 6.93; P, 11.65.

EXAMPLES 7,8

3,4-dihydro-3-methoxy-7-(octyloxy)-1H-naphth[1,8-de][1,2]oxaphosphepin 3oxide (Example 7) and 3,4-dihydro-3-methoxy-8-(octyloxy)-1H-naphth[1,-8de][1,2]oxaphosphepin 3-oxide (Example 8)

A solution of 1,8-dibromomethylene-4-(8-octyloxy)-naphthalene (Preparation 2, 12.6 g, 28 mmol) in toluene (85 ml) is treated with trimethylphosphite (7.93 ml, 8.34 g, 67.2 mmol) and heated at reflux temperature for 3 hours. The solution is evaporated and the residue is fractionated on silica gel (500 g) with ethyl acetate eluent. A 1:1 mixture of 3,4-dihydro-3-methoxy-7-(octyloxy)-1H-naphth[1,8-de][1,2]oxaphosphepin 3-oxide:3,4-dihydro-3-methoxy-8-(octyloxy)-1H-naphth[1,8-de][1,2]oxaphosphepin 3-oxide is recovered giving 0.85 g, m.p. 148°-151° C. after toluene crystallization. The remainder of the reaction mixture is reserved for further purification.

3,4-dihydro-3-methoxy-7-(octyloxy)-1H-naphth[1,8-de][1,2]oxaphosphepin 3-oxide (Example 7) and 3,4-dihydro-3-methoxy-8-(octyloxy)-1H-naphth[1,8-de][1,-2]oxaphosphepin 3-oxide (Example 8) (1:1)

IR (mull) 1600, 1435, 1365, 1295, 1265, 1255, 1195, 1170, 1080, 1020, 980, 880, 860, 840, and 785 cm$^{-1}$. MS m/z 376 (M$^+$), 280, 264, 249, 231,203, 185, 168, 152, 141, 139, and 115, NMR (CDCl$_3$) $\delta$0.89 (t, 3, CH$_3$), 1.32 (m, 8, CH$_2$), 1.53 (m, 2, CH$_2$), 1.97 (m, 2, CH$_2$), 3.69, 3.71 (d, J=10.9, 3, OCH$_3$), 3.78-4.0 (m, 2, CH$_2$—P—), 4.01 (m, 2, CH$_2$), 5.32 (q, J=13.8, 19.6, 1, CH$_2$—O—P), 5.49* (m, 1, CH$_2$—O—P), 6.70* (d, J=7.9, 0.5, ArH), 7.75 (d, J=7.9Hz, 0.5, ArH), 7.25 (q, J=2.3, 7.9, ArH), 7.27* (d, J=7.9Hz, ArH), 8.39 (m, 1, ArH) (The asterisk in this NMR section refers to resonance due to Compound 9.) Anal. Calc'd for C$_{21}$H$_{29}$O$_4$P: C, 67.00; H, 7.76; P, 8.22. Found: C, 67.18; H, 7.78; P, 7.93.

EXAMPLE 9

[[4-(octyloxy)-1,8-naphthalenediyl]bis(methylene)]bisphosphonic acid tetramethyl ester Following the procedure of Examples 7 and 8, and subsequent to the elution of the compounds of Examples 7 and 8, a later fraction gives 8.70 g of [[4-(octyloxy)-1,8-naphthalenediyl]bis(methylene)]bisphosphonic acid tetramethyl ester (m.p. 51°-52° C.) after hexane crystallization.

IR (mull) 1595, 1415, 1350, 1325, 1290, 1250, 1240, 1225, 1185, 1115, 1120, 1070, 1060, 1025, 885, 855, 830, 805, 775 and 725 cm$^{-1}$. MS m/z 500 (M$^+$), 391, 388, 387, 355, 323, 294, 293, 291, 280, 279, 265, 263, 262, 261, 245, 247, 169, and 141. NMR (CDCl$_3$) $\delta$0.89 (t, J=6.8 Hz, 3, CH$_3$), 1.27 (m, 8, CH$_2$), 1.30 (m, 2, CH$_2$), 1.89 (m, 2, CH$_2$), 3.57, 3.58 (d, J=10.7Hz, 6, OCH$_3$), 3.97 (d, J=20.3Hz, 2, CH$_2$—P—), 4.02 (d, 20.3Hz, 2, CH$_2$—P), 4.10 (t, J=6.5Hz, 2, —OCH$_2$—), 6.76 (d, J=8Hz, 1, ArH), 7.34-7.48 (m, 3, ArH), 8.38 (m, 1, ArH). Anal. Calc'd for C$_{24}$H$_{38}$O$_7$P$_2$: C, 57.60; H, 7.65; P, 12.38. Found: C, 57.81; H, 7.53; P, 12.39.

EXAMPLE 10

[1,8-naphthalenediylbis(methylene)]bisphosphonic acid tetraethyl ester

A solution of dibromomethylnaphthalene (0.628 g, 2.0 mmol) in toluene (6 ml) is treated with triethylphosphite (0.731 g, 4.4 mmol). The solution is heated at reflux temperature for 24 hours. The solution is evaporated and the residue is fractionated on silica gel (150 g). The bisphosphonic acid is eluted with 95:5 ethyl acetate:methanol to provide a substance which slowly solidifies and is crystallized from hexane to yield [1,8-naphthalenediylbis(methylene)] bisphosphonic acid tetraethyl ester (0.31 g, m.p. 55°-56° C.).

IR (mull) 1600, 1415, 1350, 1280, 1240, 1215, 1155, 1050, 1015, 970, 865, 850, 830, 805, 780, 765, 725 and 705 cm$^{-1}$. MS m/z 428(M$^+$), 413, 320, 305, 292, 277, 264, 261, 249, 235, 233, 218, 187, 169 and 153. NMR (CDCl$_3$) $\delta$1.16 (t, J=7.1Hz, 12, CH$_3$), 3.93 (m, 8, CH$_2$—O), 4.08 (d, J=21Hz, 4, CH$_2$), 7.34 (m, 2, ArH), 7.46 (m, 2, ArH), 7.75 (d, J=7.9Hz, 2, ArH).

EXAMPLE 11

[1,8-naphthalenediylbis(methylene)]bisphosphonic acid tetramethyl ester

[1,8-naphthalenediylbis(methylene)]bisphosphonic acid tetramethyl ester is a known compound prepared by making a solution containing dibromomethylnaphthalene (2.45 g, 7.8 mmol) in toluene (15 ml) and adding trimethylphosphite (2.13 g, 17.2 mmol). The solution is heated at reflux temperature for 6 hours. Cooling of the solution causes deposition of a mixture of bisphosphonic acid and oxaphosphepin. Crystallization from 2-propanol gives [1,8-naphthalenediylbis(methylene)]bisphosphonic acid tetramethyl ester (0.71 g), m.p. 168°–170° C. (J. Meinwald, J. W. Young, J. Am. Chem. Soc. 1971, 93, 725, report a m.p. of 171°–172° C.). The filtrate residue is reserved for further purification.

IR (mull) 1415, 1340, 1240, 1220, 1180, 1110, 1040, 985, 870, 860, 825, 805, 775, and 720 cm$^{-1}$. MS m/z 372 (M+), 340, 279, 278, 263, 249, 231,229, 214, 199, 187, 169, 167, 153, 152, and 141. NMR (CDCl$_3$) δ3.60 (d, J=10.7 Hz, 12, OCH$_3$), 4.08 (d, J=21.3 Hz, 4, CH$_2$), 7.39, (t, J=7.5Hz, 1, ArH), 7.47 (m, 1, ArH), 7.78 (m, 1, ArH). Anal. Calc'd for C$_{16}$H$_{22}$O$_6$P$_2$: C, 51.62: H, 5.96; P, 16.64. Found: C, 51.67; H, 6.07: P, 16.73.

EXAMPLE 12

3,4-dihydro-3-methoxy-1H-naphth-[1,8 de][1,2]oxaphosphepin 3-oxide

Following the procedure of Example 11, the combined filtrate residue is fractioned on silica gel (125 g) with 7:3 CH$_2$Cl$_2$: acetone to yield 3,4-dihydro-3-methoxy-1H-naphth-[1,8de][1,2]oxaphosphepin 3-oxide (0.57 g), m.p. 162°–163° C. after toluene crystallization, and additional [1,8-naphthalenediylbis(methylene)]bisphosphonic acid tetramethyl ester (Example 11, 0.77 g) in later fractions.

IR (mull) 1600, 1500, 1420, 1275, 1245, 1215, 1175, 1145, 1100, 1060, 1020, 1000, 975, 925, 870, 850, 830, 820, 805, 790, 775, and 760 cm$^{-1}$. MS m/z 248 (M+), 233, 203, 187, 169, 153, 152, 141, and 115. NMR (CDCl$_3$) δ3.76 (d, J=10.9Hz, 3, CH$_3$), 3.87 (q, J=16.5, 19.9Hz, 1, CH—P), 3.93 (q, J=16.5, 19.9Hz, 1, CH—P), 5.42 (q, J=13.8, 18.6Hz, 1, CH—O—P), 5.53 (q, J=13.8, 17.3, 1, CH—O—P), 7.40 (m, 2, ArH), 7.80 (d, J=7.9Hz, 1, ArH), 7.86 (q, J=7.1, 2.6Hz, 1, ArH). Anal. Calc'd for C$_{13}$H$_{13}$O$_3$P: C, 62.91; H, 5.28; P, 12.48. Found: C, 62.72; H, 5.45; P, 12.68.

EXAMPLE 13

[(3,6-dimethoxy-1,8-naphthalenediyl)bis(methylene)]-bisphosphonic acid tetramethyl ester A suspension of 5,6-dimethoxy-1,8-bis(bromomethyl)naphthalene (4.29 g, 11.47 mmol) in toluene (50 ml) is treated with trimethylphosphite (12.92 g, 104 mmol) and heated at reflux temperature for 7.5 hours. A transient product is noted after 1.5 hours. The cooled solution is filtered free of debris and the filtrate is evaporated. The residue is triturated with ether to yield [(3,6-dimethoxy-1,8-naphthalenediyl)bis(methylene) bisphosphonic acid tetramethyl ester (3.24 g, m.p. 135°–136° C.) after crystallization from toluene solution. The filtrate residue is reserved for further purification.

IR (mull) 1600, 1410, 1230, 1200, 1180, 1160, 1065 (sh), 1045(sh), 1020(sh), 1020(sh), 1000, 865, 840, 805,790, 775, and 705 cm$^{-1}$. MS m/e 432 (M+), 401, 338, 323, 309, 306, 259, 213, 212, 198, and 161. NMR (CDCl$_3$) δ3.62 (d, J=11Hz, 12, P—OCH$_3$), 3.88 (s, 6, OCH$_3$), 3.98 (d, J=21Hz, 4, CH$_2$), 6.99 (m, 4, ArH). Anal. Calc'd for C$_{18}$H$_{26}$P$_2$O$_8$: C, 50.06; H, 6.06; P, 14.33. Found: C, 49.85; H, 6.17; P, 14.42.

EXAMPLE 14

3,4-dihydro-3,6,9-trimethoxy-1H-naphth[1,8-de][1,2]oxaphosphepin 3-oxide

The filtrate residue reserved from Example 13 is purified on silica gel (275 g) using ethyl acetate to elute 3,4-dihydro-3,6,9-trimethoxy-1H-naphth[1,8-de][1,2]oxaphosphepin 3-oxide (0.26 g, m.p. 148°–149° C.) after toluene crystallization. If desired, a 9:1 ethyl acetate:methanol eluant may be used to remove additional [(3,6-dimethoxy-1,8-naphthalenediyl)bis(methylene) bisphosphonic acid tetramethyl ester (Example 13, 0.35 g).

IR (mull) 1600, 1395, 1385, 1355(sh), 1265(sh), 1245, 1225(sh), 1195, 1180, 1155, 1075, 1060, 1020, 995, 965, 930, 840, 815, 800, 775, and 725 cm$^{-1}$. MS m/z 308(M+), 293, 279, 230, 229, 212, 199, 198, 183, 171, 169, 139, 128, and 115. NMR (CDCl$_3$) δ3.64–3.84 (m, 2, CH$_2$—P—), 3.67 (d, J=11Hz, 3, P—OCH$_3$), 3.88, 3.89 (s, 3, OCH$_3$), 5.29 (q, J=13.8, 19.3Hz, 1, CH—O—P), 5.43 (q, J=13.8, 17.1Hz, 1, CH—O—P), 6.88 (d, J=2.5Hz, 2, ArH), 7.00 (t, 1, ArH), 7.04 (t, J=2.56, 1, ArH). Anal. Calc'd for C$_{15}$H$_{17}$O$_5$P: C, 58.44; H, 5.56; P, 10.05. Found: C, 57.96; H, 5.46; P, 9.99.

EXAMPLE 15

[[4-(methoxy)-3-(propyl)-1,8-naphthalenediyl]bis(methylene)]bisphosphonic acid tetramethyl ester A solution of 1,8-dibromomethylene-4-methoxy-3-propylnaphthalene (Preparation 3, 1.2 g, 3.1 mmol) in toluene (10 ml) is treated with trimethylphosphite (7.7 g, 62 mmol) and heated at reflux temperature for 1 hour. The solution is evaporated and the residue (2.2 g) is fractionated on silica gel (150 g). Ethyl acetate elution gives crude [18/19](20 mg); 95:5 ethyl acetate:methanol elution gives [[4-(methoxy)-3-(propyl)-1,8-naphthalenediyl]bis(methylene)]bisphosphonic acid tetramethyl ester (1.1g, m.p. 69°–70° C.) after hexane crystallization.

IR (mull) 1605, 1420, 1240, 1185, 1150, 1090, 1050, 1000, 915, 870, 860, 810, 800, 770, and 730 cm$^{-1}$. MS m/z 444, 429, 397, 365, 335, 321, 319, 303, 291, 227, 225, 209, 195, 183 and 154. NMR (CDCl$_3$) δ1.01 (t, J=7.3Hz, 3, CH$_3$), 1.70 (dt, J=7.5Hz, 2, CH$_2$), 2.75 (t, J=7.5Hz, 2, CH$_2$), 3.61, 3.62 (d, J=10.8Hz, 3, —P—OCH$_3$), 3.86 (s, 3, OCH$_3$), 4.01 (d, J=12.4Hz, 2, CH$_2$—P—), 4.1 (d, J=12.8Hz, 2, CH$_2$—P—), 7.31 (d, J=4.1Hz, 1, ArH), 7.41 (m, 2ArH), 8.13 (m, 1, ArH). Anal. Calc'd for C$_{20}$H$_{30}$P$_2$O$_7$: C, 54.06; H, 6.81; P, 13.94. Found: C, 53.95; H, 7.02; P, 14.17.

EXAMPLE 16

[2,3-quinoxalindiyl]bis(methylene) bisphosphonic acid tetramethyl ester

This known compound is prepared by making a solution of quinoxaline (3.16 g, 10 mmol) in hot toluene (20 ml) and treating with trimethylphosphite (2.73 g, 22 mmol). The mixture is heated at reflux temperature for 24 hours. The cooled solution deposits [2,3-quinoxalindiyl]bis(methylene) bisphosphonic acid tetramethyl ester (2.70 g, m.p. 113°–114° C.) after recrystallization from toluene. V. A. Arbuzov et al. Izvest Acad. Nauk SSSR, 1961, 1016; 1954, E 868; (Chem Abstracts (CA) 55:27352b; CA 49:13222e) report a m.p. 115°–116° C.

IR (mull) 1490, 1400, 1365, 1325, 1255, 1185, 1060, 1040, 900, 865, 850, 830, 805, 790, and 725 cm$^{-1}$. MS m/z 374(+), 343, 280, 265, 251, 235, 219, 203, 187, 169, 167, 157, 155, 129 and 109. NMR (CDCl$_3$) δ3.77 (d, J=11Hz, 12, OCH$_3$), 3.99 (d, J=22Hz, 4, CH$_2$), 7.74 (m, 2, ArH), 8.05 (m, 2, ArH). Anal. Calc'd for C$_{14}$H$_{20}$N$_2$O$_6$P$_2$: C, 44.93; H, 5.39; N, 7.48; P, 16.55. Found: C, 44.92; H, 5.64; N, 7.49; P, 16.01.

EXAMPLE 17

[1,2-bis(methylene)phenyl]bisphosphonic acid tetramethyl ester

To a solution of 2,2'-dibromo-o-xylene (21.1 g, 0.08 tool) in toluene (240 ml) is added trimethylphosphite (23 ml, 0.19 mol). The reaction mixture is heated at reflux temperature for 32 hours. The reaction is cooled and the solvent is removed at a reduced pressure to yield an oil. The oil is chromatographed on 400 g of 40–63 μm silica gel using ethyl acetate (4,2 L) and then 10% methanol-ethyl acetate. Eluted first is the bromomethylene monophosphonate. Eluted second is 1,2-bis(methylene)-phenyl]bisphosphonic acid, tetramethyl ester (23.5 g) as an oil.

NMR (CDCl$_3$, TMS) δ7.28–7.20 (m, 4H, aromatic protons), 3.65 (d, 12H, —OCH$_3$, J=11 H$_2$), 3.42 (d, 4H, —CH$_2$—P, J=20Hz). MS 322.0714, C$_{12}$H$_{20}$O$_6$P$_2$ requires 322.0735, 213, 181, 109 m/e. IR (liquid film) 2956, 1251, 1183, 1053, 1029, 1030, 881,856, 820, 800 cm$^{-1}$. Anal. Calc'd for C$_{12}$H$_{20}$O$_6$P$_2$: C, 44.73; H, 6.26; P, 19.23. Found: C, 44.63; H, 6.23; P, 19.22.

EXAMPLE 18

2,2'-bisphenylenebis(methylene)bisphosphonic acid tetramethyl ester

A solution of 2,2'-bis(bromomethyl)-1,1'-biphenyl (19.7 g, 0.058 mol), toluene (175 ml), and trimethylphosphite (17 ml, 0.14 mol) are heated at reflux temperature for 43 hours. The reaction is cooled to room temperature and the volatiles are removed at a reduced pressure to yield a yellow oil. The oil is chromatographed on 400 g of 40–63 μm silica gel using ethyl acetate (4.2 L) followed by 10% methanol-ethyl acetate. Eluted first is the bromomethylene monophosphonate as an oil (1.02 g). Eluted next is the bisphosphonate as an oil (7.03 g, 30%).

$^1$HNMR (CDCl$_3$TMS) δ7.57 (aromatic protons) 7.38–7.23 (m, 6H, aromatic protons), 3.59, 3.57 (2d, 12H, —OCH$_3$, J=11 Hz), 2.97 (m, 4H, —CH$_2$—P). IR (liquid film) 2954, 1480, 1253, 1186, 1058, 1051, 1031, 1008, 855, 831, 813, 790, 761, 623 cm$^{-1}$. MS 398 (M+), 289, 275, 199, 179, 178, 165 m/e. Anal. Calc'd for C$_{18}$H$_{24}$O$_6$P$_2$: C, 54.28; H, 6.07; P, 15.55. Found: C, 54.23; H, 6.19; P, 15.82.

EXAMPLE 19

[1,4-phenylenebis(methylene)]bisphosphonic acid tetramethyl ester

To a solution of 2,2'-dibromo-p-xylene (15.8 g, 0.06 mol) in toluene (180 ml) is added trimethylphosphite (17 ml, 0.14 mol). The reaction is heated at reflux temperature for 38 h and then cooled to room temperature. More trimethylphosphite (4.0 ml, 0.034 md is added and the reaction is refluxed for another 24 hours. The solvent and excess trimethylphosphite is removed at a reduced pressure to yield a crystalline residue. The product is recrystallized twice from ethyl acetate to yield 8.76 g (45%) of pale green crystals (MP 105.5°–106° C.).

$^1$HNMR (dc-Acetone, TMS) δ7.24 (S, 4H, aromatic protons), 3.63, 3.62 (2d, 12H, —OCH$_3$, J=11Hz), 3.17 (d, 4H, —CH$_2$—P, J=20H$_2$). IR (Nujol mull) 1511, 1261, 1247, 1203, 1182, 1046, 1025, 1016, 865, 837, 820, 806, 748 cm$^{-1}$. MS 322 (M+), 228, 213, 181, 104 m/e. Anal. Calc'd for C$_{12}$H$_{20}$O$_6$P$_2$: C, 44.73; H, 6.26; P, 19.23. Found: C, 44.79; H, 6.12; P, 19.25.

EXAMPLE 20

1,3-phenylenebis(methylene)bisphosphonic acid tetramethyl ester

A solution of 2,2'-dibromo-m-xylene (10.0, 0.038 mol) in toluene (100 ml) is mixed with trimethylphosphite (11 ml, 0.091 mol) and the solution is heated to reflux temperature. After heating at reflux for 22 h, more trimethylphosphite (5.0 ml, 0.042 mol) is added. The reaction is heated at reflux for another 12.5 hours. After cooling the reaction to room temperature, the solvent is removed at a reduced pressure to yield 14.7 g of a yellow oil. The oil is chromatographed on 400 g of 40–63 μm silica gel using ethyl acetate (2.3 L), 10% methanol-ethyl acetate (2.0 L), and 15% methanol-ethyl acetate. Eluted first is the bromomethylene monophosphonate as an oil (0.84 g). Eluted second is the bisphosphonate to yield 9.94 g (81%) as a white hygroscopic solid. The solid is recrystallized from t-butylmethyl ether pentane to give while crystals M.P. 62.5°–64° C.

$^1$HNMR (CDCl$_3$, TMS) δ7.31–7.19 (m, 4H, aromatic protons), 3.68 (d, 12H, —OCH$_3$, J=11Hz), 3.16 (d, 4H, —CH$_2$—P), J=22 Hz). MS 322.0725, C$_{12}$H$_{20}$O$_6$P$_2$ requires 322.0735, 228, 213, 199, 181, 118, 105 m/e. IR (Nujol mull) 1448, 1284, 1265, 1222, 1053, 1022, 891, 863, 835, 782, 708, cm−1. Anal. Calc'd for C$_{12}$H$_{20}$O$_6$P$_2$: C, 44.73, H, 6.26; P, 19.23. Found: C, 44.82; H, 6.17; P, 19.34.

EXAMPLE 21

[4,5-dimethyl-1,2-phenylenebis(methylene)]bisphosphonic acid tetramethyl ester

A solution of 1,2-bis(chloromethyl)-4,5-dimethylbenzene (12.18 g, 0.06 mol) in toluene (180 mL) is treated with trimethylphosphite (21 mL, 22.33 g, 0.18 mol) and then heated to reflux temperature under a nitrogen atmosphere for 18 hours.

The starting material remaines by TLC evidence. A very small amount (<10%) of a more polar spot is seen on TLC. The toluene is removed at reduced pressure, trimethyl phosphite (25 mL) is added, and the reaction is heated with an oil bath to ~170° C. for 18 hours.

The starting material is gone by TLC evidence. The reaction is cooled to room temperature and the excess trimethylphosphite is removed at a reduced pressure. The residue (an oil) is chromatographed on 400 g of 40–63 μm silica gel. The sample is applied and eluted with ethyl acetate until fraction number 50 and then with 10% methanol-ethyl acetate. Fractions which contained 50 mL each are collected. The material in fractions 67–80 crystallized and are recrystallized from ether-hexane giving the title compound (5.08 g, 0.0145 mole, 24%) as white crystals, mp 66°–69° C.

IR(mull) 1249, 1250, 1231, 1182, 1061, 1037, 892, 865, 829, 808 cm$^{-1}$. $^1$H NMR (CDCl$_3$) δ7.02 (S, 2H, aromatic), 3.66 (d, 12H, J=10.7 Hz, —OCH$_3$), 3.33 (d, 4H, J=20 Hz, —CH$_2$P—), 2.21 (s, 6H, —CH$_3$). MS $C_{14}H_{24}O_6P_2$ requires 350.1048. Found: 350.1054, 256, 241.0993, 225, 147, 133, 117, 93 m/e. Anal. calc'd for $C_{14}H_{24}O_6P_2$: C, 48.01; H, 6.91; P, 17.69. Found: C, 48.17; H, 6.91; P, 17.81.

EXAMPLE 22

[2,3-naphthalenediylbis(methylene)]bisphosphonic acid tetramethyl ester (a) 2,3-bis(hydroxymethyl)naphthalene A solution of 2,3-naphthalenedicarboxylic acid (4.6 g, 0.023 mole) in dry THF (135 mL, warmed to 50° C. to maintain solution) is added dropwise over 15 minutes to a 1.15M lithium aluminum hydride solution in THF (45 mL, 0.052 mole). The solution is stirred 3 hours after which TLC indicated consumption of diacid and formation of a new major product. The reaction is quenched carefully with THF-water, then 2N hydrochloric acid (40 mL) is added, and the resulting mixture is extracted 3 times with ether. The combined ether extracts are washed with water (2 times), with saturated sodium bicarbonate solution (1 time), with water, and are dried (sodium sulfate), filtered, and concentrated to give a tan solid (3.67 g). The solid is recrystallized from ethyl acetate giving the title compound (2.91 g) as a light tan crystalline material, mp 161°–162° C. (lit. ref mp 160° C.).

$^1$H NMR (d$_6$-acetone) $\delta$7.88, 7.47 (2m, 6H, aromatic), 4.86 (d, 4H, J=5.5 Hz, —CH$_2$—), 4.53 (t, 2H, —OH). Anal. calc'd for $C_{12}H_{12}O_2$: C, 76.57; H, 6.43. Found: C, 76.78; H, 6.35.

(b) 2,3-bis(bromomethyl)naphthalene.

A solution of CBr$_4$ (23.22 g, 0.07 mole) in acetonitrile (35 mL) is added dropwise over a period of 15 minutes to a stirred mixture of 2,3-bis(hydroxymethyl)naphthalene (Example 22(a), 2.70 g, 0.014 mole) and triphenylphosphine (10.28 g, 0.039 mole) in acetonitrile (70 mL). The reaction is warmed and midway through the addition, a clear amber colored solution is observed. After one hour, the solvent is removed under reduced pressure from the reaction and the residual solid is chromatographed (300 g of 63–200 μm silica gel, packed in hexane) by plating the solid from a methylenechloride solution onto 20 g of silica gel. The later is placed on top of the column and eluted with hexane (1 L) and with 10% EtOAc-hexane. Fractions of 50 mL volume are collected and the dibromide (2.81 g, 64%) is eluted in fractions 42–49.

$^1$H NMR (CDCl$_3$) $\delta$7.79, 7.50 (2 m, 6H, aromatic), 4.88 (s, 4H, —CH$_2$Br). $^{13}$C NMR (CDCl$_3$, ppm from TMS) 133.80, 133.34, 130.22, 127.79, 127.27, 31.09. MS 314 (M+), 233, 154 m/e.

(c) [2,3-naphthalenediylbis(methylene)]bisphosphonic acid tetramethyl ester

A flask is charged with 2,3-bis(bromomethyl)naphthalene (Example 22(b), 2.80 g, 8.9 mmol) and toluene (50 mL). The solution is heated at reflux and 25 mL of the toluene is collected in a Dean-Stark trap. The solution is then cooled to room temperature and trimethylphosphite (4.0 mL, 0.034 mol) is added. The reaction is heated to reflux temperature for 24 hours. The excess trimethylphosphite and toluene are removed at reduced pressure, giving a white solid (3.24 g). The solid is recrystallized from ethyl acetate-hexane to give 2.55 g of white crystals, mp 119.5°–120.5° C.

IR (mull) 1413, 1269, 1255, 1232, 1223, 1048, 1035, 1025, 920, 881,869, 829, 819, 802, 762 cm$^{-1}$. $^1$H NMR (CDCl$_3$) $\delta$7.77, 7.44 (2m, 6H, arom. H), 3.65 (d, 12H, P—OCH$_3$, J=10.7 Hz) 3.62 (d, 4H, —CH$_2$—P—, J=21.1 Hz). MS M+ at 372, 278, 263, 155 m/e. Anal. calc'd for $C_{16}H_{22}O_6P_2$ (372.30): C, 51.62; H, 5.96; P, 16.64. Found: C, 51.57; H, 5.86; P, 16.62.

EXAMPLE 23

[2-fluoro-1,3-phenylenebis(methylene)]bisphosphonic acid tetramethyl ester

A solution of 2,6-bis(bromomethyl)-1-fluorobenzene (2.82 g, 0.010 mole) and trimethylphosphite (5.0 mL, 0.042 mole) in toluene (25 mL) is heated at reflux temperature for 24 hours, after which the solvent and excess trimethylphosphite are removed under reduced pressure. The solid residue is crystallized from ethyl acetate-hexane, giving 3.12 g (0.0089 mole, 89%) of the title compound, mp 116.5°–117.5° C. Recrystallization gives 2.64 g, mp 117°–118° C.

IR (mull) 1448, 1413, 1288, 1278, 1266, 1226, 1184, 1149, 1088, 1076, 1053, 1023, 966, 873, 847, 782, 748, 728, 701 cm$^{-1}$.

$^1$H NMR (CDCl$_3$) is 7.25, 7.07 (m, 3H, aromatic), 3.71 (d, 12H, J=10.9 Hz. —OCH$_3$), 3.23 (d, 4H, J=21.3 Hz, ArCH$_2$P). MS 340 (M+), 320, 308, 231, 122, 109 m/e. Anal. calcd for $C_{12}H_{19}FO_6P_2$: C, 42.36; H, 5.63; F, 5.59; P, 18.21. Found: C, 42.54; H, 5.42; F, 5.50; P, 18.07.

EXAMPLE 24

[2,5-dimethyl-1,4-phenylenebis(methylene)]bisphosphonic acid tetramethyl ester

A solution of 2,5-bis(chloromethyl)-p-xylene (8.12 g, 0.04 mole) in toluene (150 mL) is refluxed one hour with azeotropic removal of water. Then trimethylphosphite (14 mL, 14.9 g, 0.12 mole) is added and the solution is heated at reflux temperature for 55 hours after which TLC shows the reaction to be incomplete. Toluene is removed, more trimethylphosphite (20 mL) is added, and the resulting solution is heated at reflux temperature for 18 hours. Excess trimethylphosphite is removed under reduced pressure leaving a white solid residue. The solid is recrystallized from ethyl acetate to give the title compound (11.03 g), mp 121°–123° C. A second recrystallization gives a colorless crystals of mp 121°–123° C.

IR (mull) 1509, 1446, 1275, 1225, 1212, 1190, 1181, 1047, 1024, 996, 893, 882, 846, 826, 778, 611 cm$^{-1}$. $^1$H NMR (CDCl$_3$) $\delta$7.07 (s, 2H, arom. H), 3.66 (d, 12H, P—OCH$_3$, J=10.6 Hz), 3.12 (d, 4H, P—CH$_2$—, J=20.5 Hz), 2.32 (s, 6H, —CH$_3$). MS $C_{14}H_{24}O_6P_2$ requires 350.1048. Found: 350.1039. Anal. calc'd for $C_{14}H_{24}P_6P_2$: C, 48.01; H, 6.91; P, 17.69. Found: C, 48.11; H, 6.90; P, 17.65.

EXAMPLE 25

[2,3,5,6-tetrachloro-1,4-phenylenebis(methylene)]bisphosphonic acid tetramethyl ester A mixture of α,α',2,3,5,6-hexachloro-p-xylene (6.26 g, 0.02 mol) in toluene (60 mL) and trimethylphosphite (7.0 mL, 7.4 g, 0.06 mol) is heated to reflux temperature. The flask is set up with a condenser, Dean-Stark trap, and the nitrogen inlet positioned so that any methyl chloride produced in the reaction will be swept out the condenser. A clear solution resultes with heating and the solution is heated at reflux for 18 hours. The toluene is distilled from the flask via the Dean-Stark trap, more trimethylphosphite is added (7.0 mL), and the reaction is heated with an oil bath (~110° C.) for 48 hours. After standing at room temperature, a white solid formed in the flask. A TLC indicated that no starting material remained. Toluene (100 mL) is added to flask and the mixture is heated at reflux temperature with stirring until a clear solution is obtained. The reaction mixture is allowed to cool to room temperature and a white precipitate formed. The white solid is collected by filtration, washed with hexane, dried in a vacuum desiccator, to give 5.17 g of title compound, mp 179°–181° C. Recrystallization from ethyl acetate gives 2.44 g as white crystals, mp 181°–182° C. There are some problems keeping the product in solution during the filtration of the hot ethyl acetate solution so that a considerable amount of material crystallized out during filtration. These crystals are combined with the filtrate from the collection of the first crop and yielded. 2.27 g. This material is recrystallized from ethyl acetate giving a second crop of 2.22 g, mp 181°–182° C.

IR (mull) 1417, 1339, 1270, 1226, 1137, 1053, 1015, 876, 861, 821, 790, 654, 632 cm$^{-1}$. MS M+ ($C_{12}H_{16}O_6P_2Cl_4$) 457.9176. Anal. calc'd for $C_{12}H_{16}Cl_4O_6P_2$: C, 31.33; H, 3.51; Cl, 30.83; P, 13.47. Found: C, 31.27; H, 3.31; Cl, 31.05; P, 13.28.

EXAMPLE 26

[1,4-naphthalenediylbis(methylene)]bisphosphonic acid tetramethyl ester (a) 1,4-naphthalenedimethanol A dry 3-neck, 1 L flask equipped with a $N_2$ inlet and dropping funnel is charged with dry THF (200 mL) and LiAlH$_4$ (1.90 g, 0.050 mole). To the stirred mixture is added via the dropping funnel a hot solution of naphthalene-1,4-dicarboxylic acid (4.32 g, 0.020 mole) in THF (200 mL) over a period of about 1 hour. The resulting mixture is stirred without heating for 90 minutes and then is heated to reflux temperature. After 2 hours, additional LiAlH$_4$ (40 mL of a 1.15M solution in THF) is added and refluxing continued for 90 minutes. The reaction is stirred at room temperature overnight, then is quenched carefully with THF-water (3:1), acidified to pH <4 with 2N hydrogen chloride, transferred to a separatory funnel and extracted (3 times) with ether. The combined ether extracts are washed with water (2 times), dried (sodium sulfate), filtered, and concentrated to give a white solid (3.68 g). The solid is crystallized from ethyl acetate-hexane, giving (2.68 g) as white crystals, mp 124°–126° C.

IR (mull) 3359, 3301, 1439, 1392, 1343, 1235, 1078, 1062, 997, 991, 850, 836, 781, 762, 747, 647, 615 cm$^{-1}$. $^1$H NMR (CDCl$_3$) δ8.14, 7.57 (2m, 4H, aromatic), 7.48 (s, 2H, C-2 and C-3 protons), 5.14 (s, 4H, —CH$_2$—). MS 188 (M+), 169, 157, 141,129 m/e. Anal. calc'd for $C_{12}H_{12}O_2$: C, 76.57; H, 6.43. Found: C, 76.54; H, 6.51.

(b) 1,4-bis(bromomethyl)naphthalene

Carbon tetrabromide (17.25 g, 0.052 mole) in acetonitrile (35 mL) is added dropwise over a period of 15 minutes to a stirred mixture of 1,4-naphthalenedimethanol (Example 26(a), 2.45 g, 0.013 mole) and triphenylphosphine (8.66 g, 0.033 mole) in acetonitrile (70 mL). The resulting dark yellow solution is stirred at room temperature for 24 hours after which TLC indicates incomplete reaction. More triphenylphosphine (0.892 g, 0.0034 mole) is added and stirring continued 24 hours. More triphenylphosphine (1.70 g, 0.0065 mole) and CBr$_4$ (4.30 g, 0.013 mole) are added. A precipitate begins to separate immediately. A TLC after one hour indicates complete reaction. Solvent is removed under reduced pressure and the solid residue is chromatographed over silica gel (400 g, 63–200 μm, hexane, 50 mL fractions) by plating the solid from a solution in acetone onto 50 g silica gel and adding this to the top of the chromatography column. Elution of the column with hexane (1 L), 30% acetone-hexane (2 L), and 40% acetone-hexane gives the product in fractions 45–62 (2.54 g, 0.0081 mole, 62%). Crystallization from acetone-hexane gives 2.21 g, as off-white crystals, mp 191°–192° C. (with some bubbling at the mp).

IR (mull) 1518, 1446, 1253, 1203, 846, 772, 756, 651 cm$^{-1}$. MS 312 (M+), 233, 154, 76 m/e. Anal. calc'd for $C_{12}H_{10}Br_2$: C, 45.90; H, 3.21; Br, 50.89. Found: C, 46.00; H, 3.16; Br, 50.28.

(c) [1,4-naphthalenediylbis(methylene)]bisphosphonic acid tetramethyl ester

A 200 mL round bottom flask is charged with 1,4-bis(bromomethyl)naphthalene (Example 26(b), 2.07 g, 6.6 mmol) and toluene (75 mL). The flask is equipped with a Dean-Stark trap, condenser, and nitrogen inlet. The mixture is heated to reflux temperature to dry the toluene and starting material. A total of 25 mL of toluene is collected in the Dean-Stark trap and then discarded. The mixture is cooled to room temperature and then trimethyl-phosphite (4 mL, 34 mmol) is added and the reaction is heated at a gentle reflux overnight. The reaction is checked by TLC after 24 hours and found to be complete. The toluene and excess trimethylphosphite are removed at a reduced pressure to yield an oil. The product is chromatographed on 400 g of 40–63 μm silica gel. The sample is applied in ethyl acetate and elution is with 10% methanol-ethyl acetate. Fractions which contained 50 mL each are collected. The desired product (2.01 g, 0.00542 mole, 81%) is eluted in fractions 60–80 and is a viscous oil.

IR (liquid film) 2955, 1281, 1252, 1216, 1183, 1057, 1028, 862, 822, 793, 767, 607 cm$^{-1}$. $^1$H NMR (CDCl$_3$) δ8.11, 7.58 (2m, 4H, aromatic), 7.45 (d, 2H, J=2.2 Hz, C-2 and C-3 protons), 3.64 (d, 4H, J=20.0 Hz, —CH$_2$P—), 3.66 (d, 12H, J=10.7 Hz, —OCH$_3$). MS $C_{16}H_{22}O_6P_2$ requires 372.0897. Found: 372.0898, 263, 231, 199, 154, 109 m/e. Anal. calc'd for $C_{16}H_{22}O_6P_2$: C, 51.62; H, 5.96; P, 16.64. Found: C, 51.11; H, 6.06; P, 16.46.

EXAMPLE 27

[2,7-naphthalenediylbis(methylene)]bisphosphonic acid tetramethyl ester (a) 2-7-bis(bromomethyl)naphthalene and 2-bromomethyl-7-dibromomethylnaphthalene A solution of 2,7-dimethylnaphthalene (3.12 g, 0.020 mole) in CCl$_4$ (250 mL) is stirred with N-bromosuccinimide (8.90 g, 0.050 mole) in a pyrex flask and is irradiated with light from a 625 watt Sylvania Sun Gun placed 10 cm from the flask. Irradiation is continued for 35 minutes with heat from the lamp causing the CCl$_4$ to reflux. Following irradiation, the solution is heated at reflux temperature for another 45 minutes, cooled, and filtered to remove undissolved solids. The solids are washed with CCl$_4$, the washings are combined with the filtered reaction solution, and this solution is concentrated under reduced pressure. The crude product is examined by $^1$H NMR which suggested a 1:1 mixture of dibromo and tribrominated products.

(b) [2,7-naphthalenediylbis(methylene)]bisphosphonic acid tetramethyl ester

The crude product from Example 27(a), a 1:1 mixture of dibromo and tribromo products (assumed to contain 0.010 mole of each), is dissolved in toluene (25 mL) and trimethylphosphite (10 mL, 0.085 mole). The mixture is heated at reflux temperature for 24 h after which excess toluene and trimethylphosphite are removed under reduced pressure. The dark red residue is chromatographed (400 g of 40–63 μm silica gel, 10% methanol in chloroform, 50 mL fractions), with fractions 31–36 containing 4.90 g of material which is rechromatographed (400 g of 40–63 μM silica gel, ethyl acetate, 50 mL fractions). The column is eluted with ethyl acetate (1 L) and then with 10% methanol in ethyl acetate. Fractions 70–92 (2.09 g) still contained two components (tlc, silica gel, 10% $CH_3OH$—$CHCl_3$, 4% $CH_3OH$—$CH_2Cl_2$) and is chromatographed (400 g of 40–63 μM silica gel, $CH_2Cl_2$, 50 mL fractions) a third time. Elution is with 4% $CH_3OH$—$CH_2Cl_2$ through fraction 80 and then with 10% $CH_3OH$—$CH_2Cl_2$. Fractions 41–47 contained the desired diphosphonate (1.418 g) as a viscous oil which slowly solidifies. Crystallization from acetone-hexane give crystals, mp 87°–88° C.

$^1$H NMR ($CDCl_3$) δ7.78, 7.71, 7.41 (3 m, 6H, aromatic), 3.68 (d, 12H, J=10.7 Hz, —$OCH_3$), 3.32 (d, 4H, J=21.8 Hz, —$CH_2P$—). MS $C_{16}H_{26}O_6P_2$ requires 372.0892. Found: 372.0893. Anal. calc'd for $C_{16}H_{26}O_6P_2$: C, 51.62; H, 5.96; P, 16.64. Found: C, 50.73; H, 6.18; P, 16.68.

EXAMPLE 28

[2,6-naphthalenediylbis(methylene)]bisphosphonic acid tetraethyl ester (a) 2,6-naphthalenedimethanol Naphthalene-2,6-dicarboxylic acid (6.49 g, 0.030 mole) is placed in a Soxhlet extraction thimble and extracted into a mixture of THF (280 mL) and $LiAlH_4$ (2.50 g, 0.066) mole by refluxing the THF and passing the condensate through the thimble. Extraction is extremely slow, so after 48 h, holes are punched in the thimble to allow the remaining diacid to wash into the reaction mixture. After heating the mixture at reflux temperature for 12 h, the excess $LiAlH_4$ is carefully quenched with THF-$H_2O$ (3:1). The resulting mixture is acidified (pH <3) with 2N HCl, transferred to a separatory funnel, and extracted 4 times with ether. The combined ether extracts are washed with water (2 times), dried (sodium sulfate), filtered, and concentrated to give a light tan solid (2.31 g). The solid is crystallized from EtOAc-hexane to give 2,6-naphthalenedimethanol (1.28 g) as crystals, mp 171°–172° C.

$^1$H NMR ($d_6$-acetone) δ7.82 (m, 4H, aromatic), 7.49 (d, 2H, J=9.7 Hz, aromatic), 4.78 (s, 4H, —$CH_2$—). MS $C_{12}H_{12}O_2$ requires 188.0837. Found: 188.0845.

(b) 2,6-bis(bromomethyl)naphthalene and 2-dibromomethyl-6-bromomethylnaphthalene A 250 mL round bottom flask is equipped with a thermometer, reflux condenser and nitrogen inlet. The flask is charged with carbon tetrachloride (150 mL) followed by 2,6-naphthalenedimethanol (Example 28(a), 1.87 g, 0.012 mol) and N-bromosuccimide (5.31 g, 0.03 mol). A 625 watt Sylvania Sun Gun movie light is placed 13 cm from the flask and used to shine light on the flask. The light is turned on for 20 minutes and then after turning the light off, the mixture is refluxed for 30 minutes (Note: The heat from the Sun Gun warmed the flask to reflux before the light is turned off.) A tlc indicated that all of the starting material is gone. The reaction mixture is cooled to ∼40° C. and then filtered to remove the succinimide. The precipitate (solids) are washed well with additional carbon tetrachloride. The combined filtrates are washed with water (2 times), dried (sodium sulfate), filtered and evaporated to give a tan solid, 4.05 g.

$^1$H NMR ($CDCl_3$) 7.83 (m, 9H, aromatic), 7.54 (m, 3H, aromatic), 6.81 (s, 1H, —$CHBr_2$), 4.65 (s, 6H, —$CH_2Br$), which is interpreted to be the result of a 1:1 mixture of dibromide and tribromide.

(c) [2,6-naphthalenediylbis(methylene)]bisphosphonic acid tetraethyl ester

A 1:1 mixture of dibromide and tribromide (Example 28(b), 3.76 g, 0.0106 mole) is dissolved in toluene (25 mL) and trimethylphosphite (15 mL, 15.78 g, 0.126 mole). The solution is heated at reflux temperature for 72 hours. The solvent and excess trimethylphosphite are removed under reduced pressure and the solid residue is chromatographed on silica gel (400 g, 40–63 μm EtOAc, 50 mL fractions) using EtOAc (1 L) and 10% $CH_3OH$— EtOAc for elution. Fractions 52–56 contained 1.588 g of material which has not been completely characterized and fractions 86–110 contained solid (1.785 g, 0.0048 mole. 90% assuming half of the starting mixture can be converted to the title compound). Recrystallization from EtOAc-hexane gives 1.63 g as tan crystals, mp 151°–153° C.

IR (mull) 1276, 1231, 1208, 1176, 1056, 1026, 907, 868, 840, 707, 654, 604 cm$^{-1}$. $^1$H NMR ($CDCl_3$) 7.77 (d, 2H, aromatic C-4 and C-8 protons), 7.73 (m, 2H, C-1 and C-5 protons), 7.43 (m, 2H, C-3 and C-7 protons), 3.68 (d, 12H, J=10.7 Hz, —$OCH_3$, 3.29 (d, 4H, J=21.4 Hz, —$CH_2P$—). MS $C_{16}H_{22}O_6P_2$ requires 372.0892. Found: 372.0880, 263, 231,154, 109 m/e. Anal. calc'd for $C_{16}H_{22}O_6P_2$: C, 51.62; H, 5.96; P, 16.64. Found: C, 51.53; H, 6.07; P, 16.70.

EXAMPLE 29

[1,2-phenylenebis(methylene)]bisphosphonic acid

A mixture of the diphosphonate methyl ester (Example 17, 1.025 g, 3.2 mmol) with 10 mL of concentrated hydrochloric acid is heated at reflux temperature for six hours. The aqueous hydrogen chloride is removed trader reduced pressure. The white solid residue is recrystallized from methanol-water to yield 554 mg (65%) of title compound as white crystals, mp >300° C.

IR (mull) 3083, 3051, 2336, 1263, 1257, 1171, 1128, 1086, 1070, 1051, 996, 962, 947, 824, 778 cm$^{-1}$. $^1$NMR ($CD_3OD$) δ7.29, 7.17 (2 m, 4H, aromatic), 3.32 (d, 4H, J≈20 Hz, —$CH_2P$—). MS (FAB) $C_8H_{12}O_6P_2$+$H_1$ requires 267.0187, found: 267.0168. Anal. calc'd for $C_8H_{12}O_6P_2$: C, 36.11; H, 4.55; P, 23.28. Found: C, 35.99; H, 4.48; P, 23.28.

EXAMPLE 30

[1,3-phenylenebis(methylene)]bisphosphonic acid

A mixture of the diphosphonate methyl ester (Example 20, 1.065 g, 3.3 mmol) with 10 mL of concentrated hydrochloric acid is heated at reflux temperature for six hours. The aqueous hydrogen chloride is removed under reduced pressure. A white solid residue is recrystallized from isopropyl alcohol to yield 743 mg of the title compound as white crystals.

IR (mull) 3050, 3030, 2466, 2316, 1603, 1589, 1545, 1486, 1444, 1404, 1397, 1367, 1291, 1260, 1231, 1207 cm$^1$. $^1$NMR ($CD_3OD$) δ7.21 (m, 4H, aromatic), 3.09 (d, 4H, J=22.1 Hz, —$CH_2P$—). MS (FAB) $C_8H_{12}O_6P_2$+$H_1$ requires 267.0187. Found: 267.0207. Anal. calcd for $C_8H_{12}O_6P_2$: C, 36.11; H, 4.55; P, 23.28. Found: C, 36.17; H, 4.24; P, 23.34.

EXAMPLE 31

[1,4-phenylenebis(methylene)]bisphosphonic acid

A mixture of bisphosphate ester (Example 19, 1.0 g, 3.1 mol) and concentrated HCl (10 ml) is heated to reflux temperature. A clear solution is obtained. The solution is heated at reflux temperature for 3.5 hours during which time a white precipitate formes. The mixture is cooled and then concentrated under reduced pressure to yield a white solid. The solid is recrystallized from water to give 520 mg of a white solid, mp >300° C.

IR (mull) 3040, 2800, 2331, 1265, 1232, 1157, 1145, 1131, 1114, 1090, 1000, 970, 943, 807 cm$^{-1}$. $^1$NMR (d6-DMSO) δ7.15 (s, 4H, aromatic), 2.91 (d, 4H, J=19.9 Hz, —CH$_2$P—). Anal. calcd for C$_8$H$_{12}$O$_6$P$_2$: C, 36.11; H, 4.55; P, 23.28. Found: C, 36.17; H, 4.49; P, 22.96.

Biological Activity

The utility of the compounds of the invention as a treatment for inflammatory disease is demonstrated by suppression of delayed-type hypersensitivity granuloma (DTH GRA) in mice. This assay is known by those skilled in the art as predictive of utility for the treatment of inflammatory conditions. This model measures the chronic aspects of immune-mediated inflammatory disease, such as the formation of inflammatory tissue resulting from cell proliferation (e.g., monocyte, macrophage, endothelium, fibroblast, lymphocyte) which is characteristic of, for instance, rheumatoid arthritis.

The procedure is described in C. J. Dunn et al., 4th International Conference on the Therapeutic Control of Inflammatory Disease, 1988. Briefly, female CF-1 mice, 25 to 30 grams, are obtained from The Upjohn Company breeding facility. DTH GRA lesions are induced in mBSA (bovine serum albumin) sensitized mice using mBSA-soaked 0.45 μM (8 mm. diameter) nitrocellulose filters (Millipore Corp., Bedford, Mass.) or 6 mm. hydroxyapatite discs. The disc or filter is implanted subcutaneously. Animals in which test compounds are administered may have lesions induced using either filters and discs, although the results show that either filters or discs are equally effective. The lesions are excised on Day 5. Wet weight (tissue and edema fluid) and dry weight (tissue) are determined for each lesion. The compounds are administered either orally or subcutaneously. When administered orally, the compound is dispersed in physiological sodium chloride solution at the time of DTH GRA induction (Day 1) and daily thereafter (Days 2,3, and 4). Mice are sacrificed 24 hours after the last dose (Day 5). When administered subcutaneously, the compound is dispersed in sterile physiological sodium chloride solution. Administration is daily as outlined above. In either case, untreated controls receive vehicle only.

Assay results for both novel and known compounds are shown in Table 1 for subcutaneous administration and in Table 2 for oral administration. All of the tested compounds suppress DTH-induced granulomas to some degree. For instance, when administered subcutaneously at 100 mg/kg, 3,4-Dihydro-3-methoxy-7-(phenylmethoxy)-1H-naphth [1,8-de][1,2]oxaphosphepin 3-oxide (Compound 3), suppresses granulomas by 29% (on a wet weight basis) and 42% (dry weight). At oral doses as low as 1 mg/kg, Compound 3 suppresses granulomas by 56% (wet weight) and 36% (dry weight). Higher oral doses, up to 100 mg/kg, show increasing suppression of 76% (wet) and 77% (dry).

In a second arthritis model, compound 3 inhibits antigen-induced polyarthritis by 9% when administered at 100 mg/kg. This assay is described in D. Brackertz et al., J. Immunol., (1977) 118, 1639 and L. Flora, Arth. & Rheum., (1979) 22, 340. In a third assay, the mycobacterium adjuvant-induced polyarthritis system described by M. B. Francis et al., Calc. Tiss. Res., (1972) 9, 109, Compound 3 exhibits no inhibition when administered at 10 mg/kg.

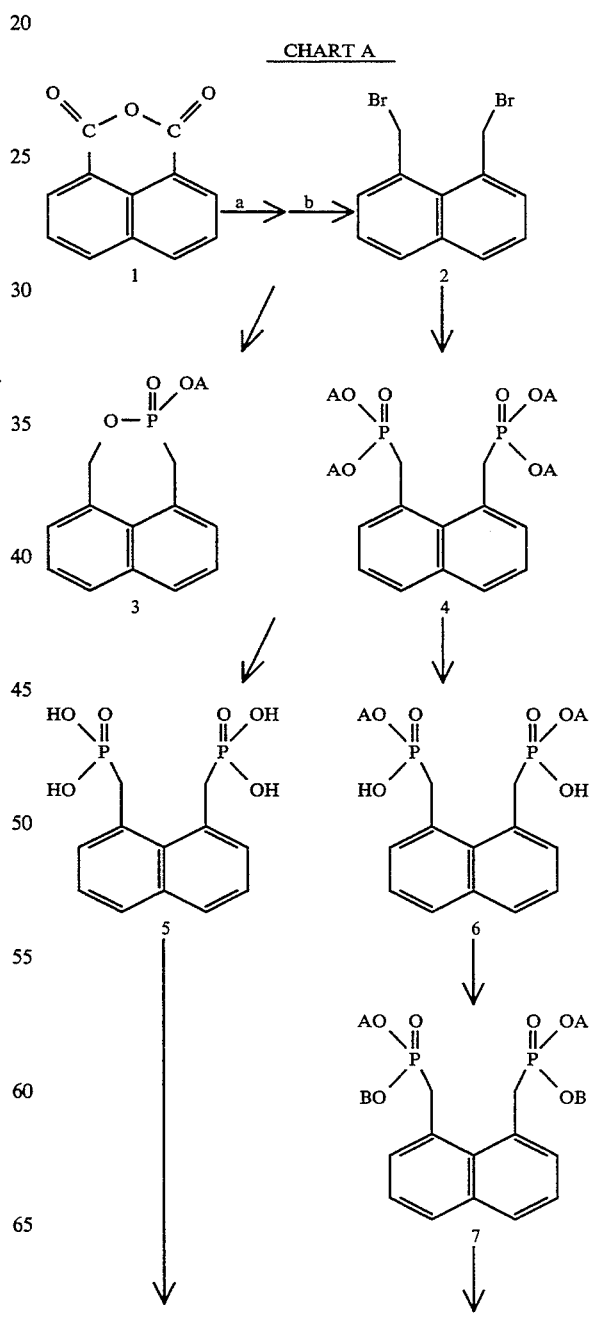

CHART A

-continued
CHART A
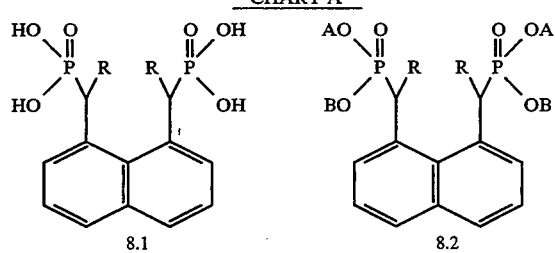
8.1     8.2
FORMULA I
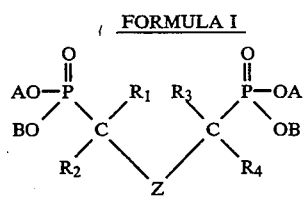    (I)
FORMULA II
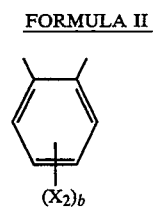    (IIa)
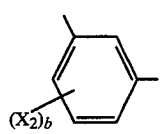    (IIb)
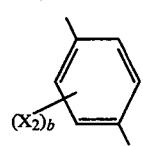    (IIc)
FORMULA III
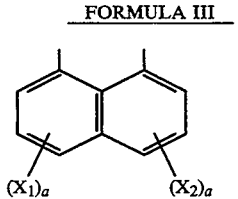    (IIIa)
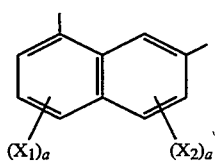    (IIIb)
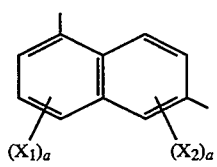    (IIIc)
-continued
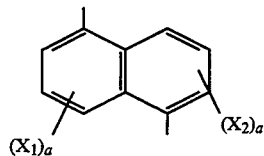    (IIId)
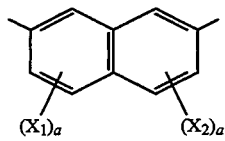    (IIIe)
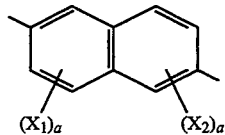    (IIIf)
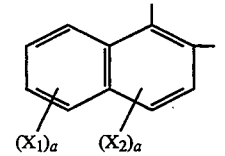    (IIIg)
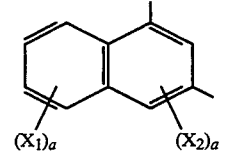    (IIIh)
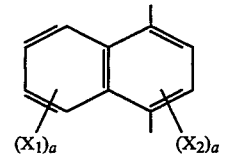    (IIIi)
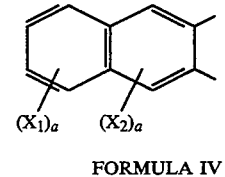    (IIIj)
FORMULA IV
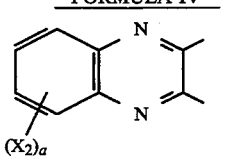    (IV)
FORMULA V
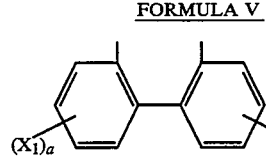    (Va)
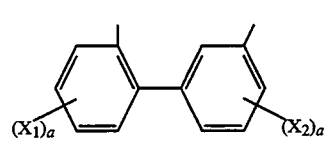    (Vb)

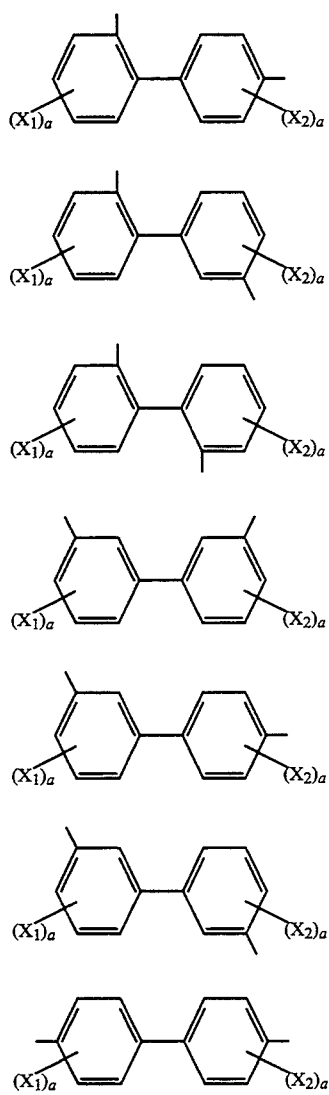

(Vc)
(Vd)
(Ve)
(Vf)
(Vg)
(Vh)
(Vi)

FORMULA VII

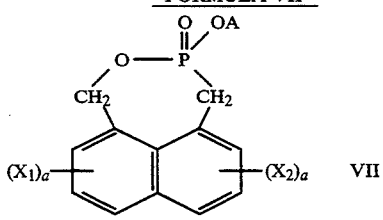

VII

TABLE 1

Subcutaneous Administration

| | | | DTH Granuloma Assay % Change from Control | |
|---|---|---|---|---|
| Example | Type | Dose (mg/kg) | Wet Wt. | Dry Wt. |
| 2 | 1,5-bisphosphonate | 100$^b$ | −35 | −40 |
| | | 100$^a$ | −17 | −36 |
| 3 | oxaphosphepin | 100$^b$ | −29 | −43 |
| | | 100$^a$ | −36 | −48 |
| 16 | 1,4-bisphosphonate | 100$^b$ | −34 | −25 |
| | | 100$^a$ | −13 | −36 |
| 19 | 1,6-bisphosphonate | 10$^b$ | — | −40 |

TABLE 1-continued

Subcutaneous Administration

| | | | DTH Granuloma Assay % Change from Control | |
|---|---|---|---|---|
| Example | Type | Dose (mg/kg) | Wet Wt. | Dry Wt. |
| 26 | 1,6-bisphosphonate | 10$^b$ | — | −71 |
| 28 | 1,8-bisphosphonate | 10$^b$ | — | −53 |

$^a$ = induction of DTH granuloma using hydroxyapatite discs.
$^b$ = induction of DTH granuloma using nitrocellulose filters.

TABLE 2

Oral Administration$^a$

| | | | DTH Granuloma Assay % Change from Control | |
|---|---|---|---|---|
| Example | Type | Dose (mg/kg) | Wet Wt. | Dry Wt. |
| 2 | 1,5-bisphosphonate | 1 | −6 | −14 |
| | | 1 | −36 | −30 |
| | | 10 | −37 | −30 |
| | | 10 | −28 | −28 |
| | | 100 | −64 | −63 |
| | | 100 | −43 | −36 |
| | | 100 | −22 | −30 |
| 3 | oxaphosphepin | 1 | −56 | −37 |
| | | 10 | −61 | −47 |
| | | 100 | −73 | −74 |
| | | 100 | −76 | −77 |
| | | 100 | −34 | −35 |
| 6 | 1,5-bisphosphonate | 100 | −24 | −27 |
| 5 | oxaphosphepin | 10 | 20 | 15 |
| 7 | 1,5-bisphosphonate | 100 | −36 | −26 |
| 8:9$^b$ | oxaphosphepin | 100 | −31 | −43 |
| 11 | 1,5-bisphosphonate | 100 | −36 | −44 |
| 13 | 1,5-bisphosphonate | 100 | −38 | −25 |
| 15 | 1,5-bisphosphonate | 100 | −29 | −40 |
| 16 | 1,4-bisphosphonate | 100 | −65 | −62 |

$^a$ = induction of DTH granuloma using nitrocellulose filters
$^b$ = a 1:1 mixture of compounds 8 and 9.

We claim:

1. A method for treating arthritic disease comprising: administering to a human in need thereof an effective amount of a compound of Formula I

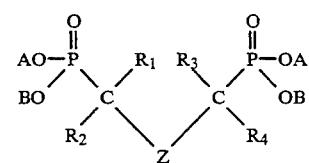

wherein $R_1$, $R_2$, $R_3$, and $R_4$ may be the stone or different, may form a quaternary carbon, and are hydrogen or $C_1$–$C_5$ alkyl;

A and B may be the same or different and are hydrogen, $C_1$–$C_6$ alkyl, phenyl, or $C_7$–$C_{10}$ aralkyl;

A and B taken together are $C_2$ cycloalkyl, $C_3$ cycloalkyl, or the alkyl-substituted derivatives thereof;

Z is a substituted benzene ring of Formula II

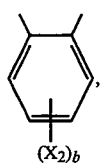 (IIa)
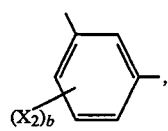 (IIb)
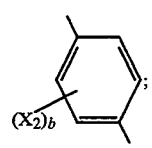 (IIc)
a substituted naphthalene ring of Formula III
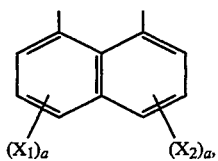 (IIIa)
(IIIb)
(IIIc)
(IIId)
(IIIe)
(IIIf)
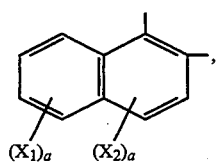 (IIIg)
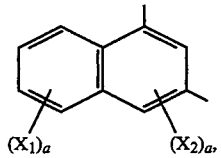 (IIIh)
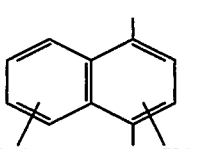 (IIIi)
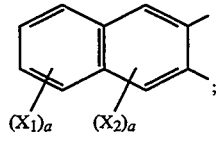 (IIIj)
a 2,3 substituted quinoxaline ring of formula IV
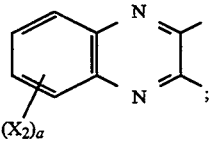 (IV)
or a substituted biphenyl of formula V
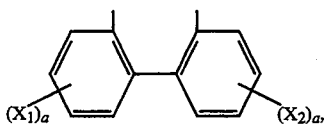 (Va)
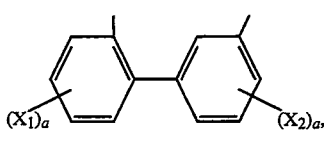 (Vb)
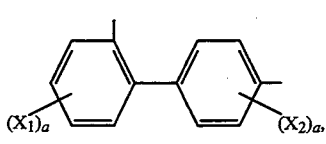 (Vc)
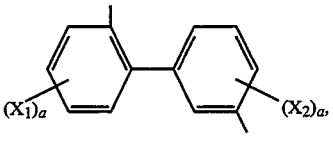 (Vd)

-continued

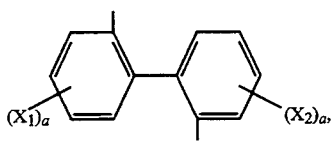
(Ve)

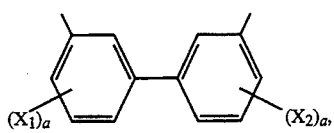
(Vf)

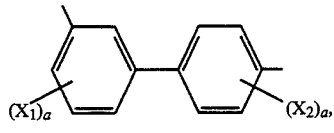
(Vg)

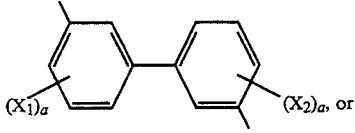
(Vh)

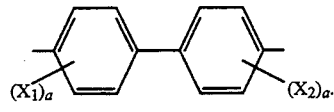
(Vi)

$X_1$ and $X_2$ may be the same or different and are hydrogen, —Cl, —Br, —F, $C_1$–$C_3$ alkyl, —$OR_5$, —$(CH_2)_mCO_2A$, —$(CH_2)_mCH_2OR_5$, —$NO_2$, —$NH_2$, —$SR_6$, —$CH_2NHR_7$, or —$CH_2N(R_7)(R_8)$;

a is one or two, provided that a is one when either $X_1$ or $X_2$ is —$NO_2$;

b is one to four, provided that b is one when $X_2$ is —$NO_2$;

$R_5$ is hydrogen, $C_1$–$C_{10}$ alkyl, allyl, $C_1$–$C_6$ acyl, benzoyl, or $C_7$–$C_{10}$ aralkyl:

$R_6$ is hydrogen, $C_1$–$C_6$ alkyl, phenyl, $C_1$–$C_6$ acyl, benzoyl, or $C_7$–$C_{10}$ aralkyl;

$R_7$ and $R_8$ may be the same or different and are hydrogen, $C_1$–$C_6$ alkyl, phenyl, $C_1$–$C_6$ acyl, benzoyl, or $C_7$–$C_{10}$ aralkyl;

m is one to five;

or the pharmacologically acceptable salts thereof.

2. The method of claim 1 wherein
Z is formula II;
A and B are hydrogen or $C_1$–$C_6$ alkyl; and
$R_1$, $R_2$, $R_3$, and $R_4$ are hydrogen.

3. The method of claim 2 wherein the compound is
{1,2-phenylenebis(methylene)}bisphosphonic acid tetramethyl ester,
{1,3-phenylenebis(methylene)}bisphosphonic acid tetramethyl ester,
{1,3-phenylenebis(methylene)}bisphosphonic acid,
{4,5-dimethyl-1,2-phenylenebis(methylene)}bisphosphonic acid tetramethyl ester.
{2-fluoro-1,3-phenylenebis(methylene)}bisphosphonic acid tetramethyl ester.
{1,4-phenylenebis(methylene)}bisphosphonic acid tetramethyl ester,
{2,5-dimethyl-1,4-phenylenebis(methylene)}bisphosphonic acid tetramethyl ester,
{2,3,5,6-tetrachloro-1,4-phenylenebis(methylene)} bisphosphonic acid tetramethyl ester.
{1,2-phenylenebis(methylene)}bisphosphonic acid, or
{1,4-phenylenebis(methylene)}bisphosphonic acid.

4. The method of claim 1 wherein
Z is formula III;
A and B are hydrogen or $C_1$–$C_6$ alkyl; and
$R_1$, $R_2$, $R_3$, and $R_4$ are hydrogen.

5. The method of claim 4 wherein the compound is
{1,8-naphthalenediyl}bis(methylene)bisphosphonic acid tetraethyl ester,
{1,8-naphthalenediylbis(methylene)}bisphosphonic acid tetramethyl ester,
{2,3-naphthalenediylbis(methylene)}bisphosphonic acid tetramethyl ester,
{1,4-naphthalenediylbis(methylene)]bisphosphonic acid tetramethyl ester,
{2,7-naphthalenediylbis(methylene)}bisphosphonic acid tetramethyl ester,
{2,6-naphthalenediylbis(methylene)}bisphosphonic acid tetraethyl ester,
{4-(octyloxy)-1,8-naphthalenediylbis(methylene)} bisphosphonic acid tetramethyl ester,
{4-(phenylmethoxy)-1,8-naphthalenediylbis(methylene)}bisphosphonic acid tetramethyl ester,
{4-(phenylmethoxy)-1,8-naphthalenediylbis(methylene)}bisphosphonic acid tetraethyl ester,
{3,6-(dimethoxy)-1,8-naphthalenediylbis(methylene)}bisphosphonic acid tetramethyl ester, or
{4-(methoxy)-3-(propyl)-1,8-naphthalenediylbis(methylene)}bisphosphonic acid tetramethyl ester.

6. The method of claim 1 wherein
Z is formula IV;
A and B are hydrogen or $C_1$–$C_6$ alkyl; and
$R_1$, $R_2$, $R_3$, and $R_4$ are hydrogen.

7. The method of claim 6 wherein the compound is
{2,3-quinoxalindiyl}bis(methylene) bisphosphonic acid tetramethyl ester.

8. The method of claim 1 wherein
Z is formula V;
A and B are hydrogen or $C_1$–$C_6$ alkyl; and
$R_1$, $R_2$, $R_3$, and $R_4$ are hydrogen.

9. The method of claim 8 wherein the compound is
{2,2'-biphenylenebis(methylene)}bisphosphonic acid tetramethyl ester.

* * * * *